(12) United States Patent
Furukawa et al.

(10) Patent No.: US 9,441,009 B2
(45) Date of Patent: *Sep. 13, 2016

(54) CO-MODIFIED ORGANOPOLYSILOXANE, AND POWDER TREATMENT AGENT AND POWDER COMPOSITION COMPRISING THE SAME

(71) Applicant: DOW CORNING TORAY CO., LTD., Tokyo (JP)

(72) Inventors: Haruhiko Furukawa, Chiba (JP); Akito Hayashi, Chiba (JP); Tomohiro Iimura, Chiba (JP)

(73) Assignee: DOW CORNING TORAY CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/433,195

(22) PCT Filed: Oct. 2, 2013

(86) PCT No.: PCT/JP2013/076811
§ 371 (c)(1),
(2) Date: Apr. 2, 2015

(87) PCT Pub. No.: WO2014/054686
PCT Pub. Date: Apr. 10, 2014

(65) Prior Publication Data
US 2015/0239924 A1    Aug. 27, 2015

(30) Foreign Application Priority Data

Oct. 2, 2012   (JP) ................. 2012-220287

(51) Int. Cl.
| | |
|---|---|
| *C07F 7/08* | (2006.01) |
| *C07H 23/00* | (2006.01) |
| *A61K 8/898* | (2006.01) |
| *C08G 77/38* | (2006.01) |
| *C08L 83/14* | (2006.01) |
| *A61Q 19/00* | (2006.01) |
| *A61K 8/02* | (2006.01) |
| *A61Q 1/10* | (2006.01) |
| *A61Q 1/08* | (2006.01) |
| *A61Q 1/12* | (2006.01) |
| *C08G 77/50* | (2006.01) |
| *A61Q 1/02* | (2006.01) |
| *A61Q 1/06* | (2006.01) |
| *A61Q 17/04* | (2006.01) |

(52) U.S. Cl.
CPC ............ *C07H 23/00* (2013.01); *A61K 8/022* (2013.01); *A61K 8/898* (2013.01); *A61Q 1/08* (2013.01); *A61Q 1/10* (2013.01); *A61Q 1/12* (2013.01); *A61Q 19/00* (2013.01); *C08G 77/38* (2013.01); *C08L 83/14* (2013.01); *A61K 2800/10* (2013.01); *A61K 2800/43* (2013.01); *A61K 2800/54* (2013.01); *A61K 2800/651* (2013.01); *A61K 2800/652* (2013.01); *A61K 2800/654* (2013.01); *A61Q 1/02* (2013.01); *A61Q 1/06* (2013.01); *A61Q 17/04* (2013.01); *C08G 77/50* (2013.01)

(58) Field of Classification Search
USPC ................. 556/430, 445, 449, 450
See application file for complete search history.

(56) References Cited

U.S. PATENT DOCUMENTS

| | | | |
|---|---|---|---|
| 4,591,652 A | 5/1986 | DePasquale et al. | |
| 4,661,577 A | 4/1987 | Jo Lane et al. | |
| 5,831,080 A | 11/1998 | Sejpka et al. | |
| 5,891,977 A | 4/1999 | Dietz et al. | |
| 6,517,933 B1 | 2/2003 | Soane et al. | |
| 9,133,309 B2 * | 9/2015 | Iimura | A61Q 19/00 |
| 2003/0185771 A1 | 10/2003 | Kamei et al. | |
| 2004/0186308 A1 | 9/2004 | Koch et al. | |
| 2005/0043365 A1 | 2/2005 | Yoshitake et al. | |
| 2008/0209645 A1 | 9/2008 | Carrillo et al. | |
| 2010/0266651 A1 * | 10/2010 | Czech et al. | 424/401 |
| 2011/0027213 A1 | 2/2011 | Kamei et al. | |
| 2011/0182846 A1 | 7/2011 | Ikeda et al. | |
| 2012/0251605 A1 | 10/2012 | Iimura et al. | |
| 2012/0263662 A1 | 10/2012 | Iimura et al. | |
| 2012/0269747 A1 * | 10/2012 | Iimura | A61Q 19/00 424/59 |
| 2012/0269875 A1 | 10/2012 | Tamura et al. | |
| 2013/0096206 A1 | 4/2013 | Iimura et al. | |
| 2013/0102686 A1 | 4/2013 | Tamura et al. | |
| 2013/0149261 A1 * | 6/2013 | Delvalle | A61K 8/06 424/49 |

(Continued)

FOREIGN PATENT DOCUMENTS

| | | |
|---|---|---|
| JP | 62-068820 A | 3/1987 |
| JP | S63-139106 A | 6/1988 |

(Continued)

OTHER PUBLICATIONS

PCT/JP2013/076811 International Search Report dated Dec. 24, 2013, 3 pages (In Japanese).

(Continued)

*Primary Examiner* — Pancham Bakshi
(74) *Attorney, Agent, or Firm* — Warner Norcross & Judd LLP

(57) ABSTRACT

A co-modified organopolysiloxane having a group having a siloxane dendron structure and a group containing a saccharide component (e.g. a sugar lactone amide alkyl group) is disclosed. The present invention also provides a method for producing the co-modified organopolysiloxane, as well as a surface treatment agent, a powder treatment agent, a powder composition, a powder-in-oil dispersion, a preparation for external use, and the like containing the co-modified organopolysiloxane.

20 Claims, No Drawings

(56) References Cited

U.S. PATENT DOCUMENTS

2013/0210930 A1    8/2013    Souda et al.
2014/0004065 A1    1/2014    Souda et al.
2014/0371330 A1   12/2014    Hayashi et al.

FOREIGN PATENT DOCUMENTS

| | | |
|---|---|---|
| JP | H05-186596 A | 7/1993 |
| JP | H07-053326 A | 2/1995 |
| JP | H08-269204 A | 10/1996 |
| JP | H10-167946 A | 6/1998 |
| JP | 2010-280741 A | 12/2010 |
| JP | 2011-26493 A | 2/2011 |
| JP | 2011-148784 A | 8/2011 |
| JP | 2011-149017 A | 8/2011 |
| JP | 2011-246704 A | 12/2011 |
| JP | 2011-246705 A | 12/2011 |
| JP | 2011-246706 A | 12/2011 |
| WO | WO9429324 A1 | 12/1994 |
| WO | WO02/088456 A1 | 11/2002 |
| WO | WO2007/109240 A2 | 9/2007 |
| WO | WO2009/006091 A2 | 1/2009 |
| WO | WO2009/022621 A1 | 2/2009 |
| WO | WO2011/028765 A1 | 3/2011 |
| WO | WO2011/028770 A1 | 3/2011 |
| WO | WO2011/049246 A1 | 4/2011 |
| WO | WO2011049248 A1 | 4/2011 |
| WO | WO2011/136394 A1 | 11/2011 |

OTHER PUBLICATIONS

English language abstract for JP62-068820A extracted from https://www4.j-platpat.inpit.go.jp database on Jun. 8, 2015, 1 page.

English language abstract for JP63-139106A extracted from https://www4.j-platpat.inpit.go.jp database on May 27, 2015, 2 pages.

English language abstract and machine assisted English translation for JPH05-186596A extracted from https://www4.j-platpat.inpit.go.jp database on Jun. 15, 2015, 26 pages.

English language abstract for WO9429324A1 extracted from https://www4.j-platpat.inpit.go.jp database on Jun. 15, 2015, 2 pages.

English language abstract and machine assisted English translation for JPH07-053326A extracted from https://www4.j-platpat.inpit.go.jp database on Jun. 15, 2015, 11 pages.

English language abstract and machine assisted English translation for JPH08-269204A extracted from https://www4.j-platpat.inpit.go.jp database on Jun. 15, 2015, 20 pages.

English language abstract and machine assisted English translation for JPH10-167946A extracted from https://www4.j-platpat.inpit.go.jp database on Jun. 8, 2015, 13 pages.

English language abstract and machine assisted English translation for JP2010-280741A extracted from https://www4.j-platpat.inpit.go.jp database on Jun. 15, 2015, 29 pages.

PCT/JP2013/076811 International Search Report dated Dec. 24, 2013, 2 pages. (In English).

\* cited by examiner ial Patent Application No. PCT/JP2013/076811, filed on Oct. 2,
CO-MODIFIED ORGANOPOLYSILOXANE, AND POWDER TREATMENT AGENT AND POWDER COMPOSITION COMPRISING THE SAME

CROSS-REFERENCE TO RELATED APPLICATIONS

This application is the National Stage of International Patent Application No. PCT/JP2013/076811, filed on Oct. 2, 2013, which claims priority to and all advantages of Japanese Patent Application No. 2012-220287, filed on Oct. 2, 2012, the content of which is hereby incorporated by reference.

TECHNICAL FIELD

The present invention relates to a novel co-modified organopolysiloxane copolymer which can be produced easily at a relatively low cost, the co-modified organopolysiloxane copolymer comprising a group having a carboxydendron structure in the molecule and a group having a saccharide component as a hydrophilic group, and a surface treatment agent—a powder treatment agent, in particular—containing the same. Additionally, the present invention relates to a powder that is surface treated using the powder treatment agent, a powder composition comprising the co-modified organopolysiloxane copolymer, and a powder-in-oil dispersion comprising an oil agent; and, moreover a preparation for external use, particularly a make-up cosmetic composition, comprising the same.

BACKGROUND ART

Various powders exemplified by white and colored pigments such as titanium oxide, zinc oxide, red iron oxide, and the like and extender pigments such as mica, sericite, and the like are widely used in the fields of basic cosmetic compositions and other various cosmetic compositions such as sunscreens, nail colors, nail coats, foundations, mascaras, eye liners, and the like. However, untreated powder is prone to agglomerate due to the electric charge and polarity, trace amount of impurities, and the like on the powder surface. Therefore, powders that have been subject to various surface treatments are widely used for the purpose of enhancing dispersibility and stability of a powder in a cosmetic composition and also improving the tactile sensation, moisture resistance, sebum resistance, and the like of a cosmetic composition comprising a powder.

Known examples of such surface treatments include lipophilization treatments using an oil agent, a metal soap, or the like; hydrophilization treatments using a surfactant, water-soluble polymer, or the like; hydrophobization treatments using silicone compounds; silica treatments; alumina treatments; and the like. Particularly, in recent years, there have been many cases where a surface treatment using a silicone compound having a reactive moiety in the molecule have been performed. The reactive moiety forms a chemical bond with the powder surface and, as a result, the surface treatment using the silicone compound is effective from the perspective of simultaneously modifying the surface of the powder and blocking the surface activity of the powder. Additionally, because surface treatment can be thoroughly performed, the surface treatment agent will not separate from the powder surface, even when compounded in a cosmetic composition comprising a solvent. Moreover, changes in properties of the powder due to the surface treatment can be kept to a minimum. An example of such a surface treatment is a method in which a powder is surface treated using a methylhydrogenpolysiloxane (Patent Document 1). However, in this method, unreacted Si—H groups still remain even after the surface treating of the powder and, therefore, there is a problem when this powder is compounded in a cosmetic composition because hydrogen gas may be produced depending on the components and the like in the cosmetic composition.

On the other hand, methods for manufacturing a powder dispersion using a hydrophilic modified organopolysiloxane that has good compatibility with the powder surface have been proposed. Examples thereof include a method for forming a polyether-modified organopolysiloxane into a powder dispersing aid (Patent Document 2) and a method for forming an organopolysiloxane modified by polyglycerine or a similar polyhydric alcohol into a powder dispersing aid (Patent Document 3). However, there are problems in that the powder dispersion effectiveness is still insufficient, viscosity of a power dispersion obtained by dispersing a powder in silicone oil or a similar oil agent increases gradually over time, fluidity is lost, and the like.

As a method to resolve the problems described above, the present applicant has proposed methods using a co-modified organopolysiloxane copolymer having a group that has a carbosiloxy dendron structure and a glycerin derivative, polyhydric alcohol, or similar hydrophilic group in the molecule (Patent Documents 4, 5, 6, and 7). Such co-modified organopolysiloxanes are safe and do not produce hydrogen, and can be advantageously used in the surface treating of a powder. Moreover, affinity with other raw materials of cosmetic compositions is superior, and the dispersibility and stability of the powder in a cosmetic composition comprising a powder can be enhanced.

However, although the co-modified organopolysiloxane copolymers disclosed in Patent Documents 4 to 7 are outstanding from the perspective of performance, polyglycerine groups, xylitol groups, and the like are problematic in that they are relatively expensive to produce, which has a substantial cost impact on the final product. Therefore, there is a demand for a surface treatment agent, a cosmetic raw material, and a cosmetic containing the same which have surface treatment performance equal or superior to that of these co-modified organopolysiloxane copolymers and can be produced at low cost.

On the other hand, organopolysiloxanes having modified groups containing saccharide components consisting of saccharides and sugar derivatives in the molecule, reactions for obtaining the organopolysiloxanes, and the use thereof in cosmetics have long been known (for example, Patent Documents 8 to 13). Since these modified groups containing saccharide components can be synthesized with a simple method using simple amino-modified silicone and inexpensive sugar lactones, the cost is low, and a wide variety of sugar-modified silicones can be derived by using various sugar lactones. However, the applications thereof are still limited, and the substances have only been used as certain types of surfactants such as surface treatment agents or gelling agents. In addition, there are problems in that the performance as a surface treatment agent is still insufficient, and the viscosity of a powder dispersion obtained by dispersing a powder in an oil agent such as silicone oil increases gradually over time, which leads to a loss of fluidity. Further, in these references, there is no disclosure of a co-modified organopolysiloxane having a modified group containing a saccharide component as a functional group independent of a siloxane dendron structure in the molecule, and in particular, there is no disclosure that the molecular chain length or modification rate is selected in order to improve the surface treatment performance.

The present applicants have proposed an organopolysiloxane having a sugar residue at a terminal or the like of a siloxane dendron structure (Patent Document 14). However, in these references, there is no disclosure of a co-modified organopolysiloxane having a modified group containing a saccharide component as a functional group independent of a siloxane dendron structure in the molecule, and there is no mention or suggestion of the performance or the like as a surface treatment agent. Further, these substances are completely different inventions from the inventions of this application in that in order to modify the siloxane dendron structure serving as the organopolysiloxane hydrophobic functional group disclosed in this reference with a hydrophilic group, it is necessary to introduce a sugar residue into a raw material intermediate by means of a multistage reaction (see paragraph 0014), which leads to the problem that the substances cannot be produced at low cost.

PRIOR ART DOCUMENTS

Patent Documents

Patent Document 1: Japanese Unexamined Patent Application Publication No. H07-53326A (Japanese Patent No. 2719303B)
Patent Document 2: Japanese Unexamined Patent Application Publication No. H10-167946A
Patent Document 3: Japanese Unexamined Patent Application Publication No. 2002-038013A
Patent Document 4: WO/2011/049246
Patent Document 5: WO/2011/049248
Patent Document 6: WO/2011/136394
Patent Document 7: Japanese Patent Application No. 2011-286973 (unpublished at the time of this application)
Patent Document 8: Japanese Unexamined Patent Application Publication No. S62-068820A
Patent Document 9: Japanese Unexamined Patent Application Publication No. S63-139106A
Patent Document 10: Japanese Unexamined Patent Application Publication No. H08-269204A
Patent Document 11: Japanese Unexamined Patent Application Publication No. H10-330489A
Patent Document 12: Japanese Unexamined Patent Application Publication (Translation of PCT Application) No. H05-186596A
Patent Document 13: Japanese Unexamined Patent Application Publication (Translation of PCT Application) No. 2008-545838A
Patent Document 14: Japanese Unexamined Patent Application Publication No. 2003-146991A

SUMMARY OF INVENTION

Technical Problem

Further, the present inventors discovered new problems regarding organopolysiloxanes having modified groups containing saccharide components in the molecule. As described in the background art, modified groups containing saccharide components can be synthesized with a simple method using simple amino-modified silicone and inexpensive sugar lactones, but since amino groups are highly reactive, they cannot be easily co-modified using different types of hydrophobic functional groups. Therefore, on an industrial scale, in particular, it has been difficult to synthesize co-modified organopolysiloxanes having the desired hydrophobic functional groups in addition to modified groups containing saccharide components with conventional production methods.

An object of the present invention is to provide a novel co-modified organopolysiloxane by which the problems described above can be resolved. More specifically, an object of the present invention is to provide a co-modified organopolysiloxane which can be produced at a lower cost than conventional co-modified silicones, easily synthesized on an industrial scale, has high powder dispersibility and excellent compatibility with a wide variety of cosmetic raw materials, and can be advantageously used as a cosmetic raw material. A second object of the present invention is to provide a powder treatment agent comprising the organopolysiloxane, a powder that is surface treated using the powder treatment agent, a powder composition comprising the co-modified organopolysiloxane copolymer, and a powder-in-oil dispersion comprising an oil agent; and, moreover an external use preparation, particularly a make-up cosmetic composition, comprising the same.

Solution to Problem

As a result of intensive investigation aimed at achieving the above objects, the present inventors arrived at the present invention. That is, the object of the present invention is achieved by a novel co-modified organopolysiloxane having a group that has a carbosiloxy dendron structure and a hydrophilic group such as a sugar or a sugar derivative in the molecule. In particular, the object can be advantageously achieved by a novel co-modified organopolysiloxane having a group having a carbosiloxy dendron structure and a sugar lactone amide alkyl group in the molecule.

Similarly, the object of the present invention is particularly advantageously achieved by a method for producing a novel co-modified organopolysiloxane by co-hydrosilylating a compound having a siloxane dendron structure, a compound having a functional group that can react with a compound having a saccharide component after a deprotection reaction, and an organohydrogenpolysiloxane to obtain a co-modified organopolysiloxane intermediate, performing a deprotection reaction on the intermediate, and then reacting the intermediate with a compound having a saccharide component.

In addition, the object of the present invention is achieved by a surface treatment agent—a powder treatment agent, in particular—containing a novel co-modified organopolysiloxane. Further, the object of the present invention is achieved by a powder that is surface treated using the powder treatment agent, a powder composition comprising the co-modified organopolysiloxane, and a powder-in-oil dispersion comprising an oil agent; and, moreover an external use preparation, particularly a make-up cosmetic composition, comprising the same.

Specifically, the object described above is achieved by:
[[1] a co-modified organopolysiloxane having a group ($L^1$) having a siloxane dendron structure and a group (Q) containing a saccharide component represented by the following general formula (1):

$$R^1{}_a R^2{}_b L^1{}_c Q_d SiO_{(4-a-b-c-d)/2} \qquad (1)$$

{wherein, in the general formula (1),
$R^1$ is a substituted or unsubstituted monovalent hydrocarbon group having from 1 to 30 carbon atoms, or a hydrogen atom;

$R^2$ is a substituted or unsubstituted straight-chain or branched monovalent hydrocarbon group having from 6 to 30 carbon atoms, or a chainlike organosiloxane group represented by the following general formula (2-1);

[Formula 1]

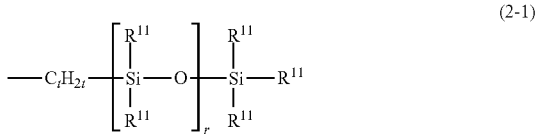

(2-1)

(wherein $R^{11}$ is a substituted or unsubstituted monovalent hydrocarbon group having from 1 to 30 carbon atoms, a hydroxyl group, or a hydrogen atom, at least one of the $R^{11}$ moieties being the monovalent hydrocarbon group; t is a number in a range of 2 to 10; and r is a number in a range of 1 to 500); or the general formula (2-2) below:

[Formula 2]

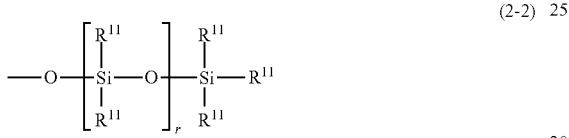

(2-2)

(wherein $R^{11}$ and r are as described above);
$L^1$ is a silylalkyl group having a siloxane dendron structure expressed by the following general formula (3) when i=1;
General Formula (3):

[Formula 3]

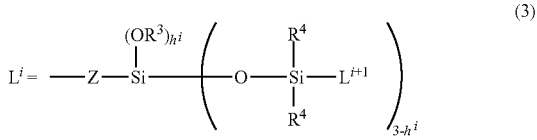

(3)

(wherein $R^3$ represents a substituted or unsubstituted, straight or branched monovalent hydrocarbon group having from 1 to 30 carbon atoms; $R^4$ each independently represents an alkyl group having from 1 to 6 carbon atoms or phenyl group; Z represents a divalent organic group; i represents a generation of the aforementioned silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and $R^4$ when i=k, and $h^i$ is a number in a range from 0 to 3);

Q is a group containing a saccharide component having the formula $X\text{-}(G^1)_n\text{-}(G^2)_m$, wherein $G^1$ in the formula is a saccharide component having from 5 to 12 carbon atoms; n+m is from 1 to 10;

and n or m may be 0, $G^2$ is a saccharide component having from 5 to 12 carbon atoms which may be additionally substituted with an organic or organic silicon group;

X is a linking group independently selected from a group consisting of the following:
—$R^5$—NHC(O)—$R^6$—;
—$R^5$—NHC(O)O—$R^6$—;
—$R^5$—NH—C(O)—NH—$R^6$—;
—$R^5$—O—$R^6$—;
—$R^5$—CH(OH)—$CH_2$—O—$R^6$—;
—$R^5$—S—$R^6$—;
—$R^5$—CH(OH)—$CH_2$—NH—$R^6$—; and
—$R^5$—N($R^1$)—$R^6$—;

wherein $R^5$ and $R^6$ are divalent spacer groups containing $(R^a)_u$, $(R^b)_v$, and $(R^c)_x$, where at least one of u, v, and x must be 1; $R^a$ and $R^c$ are alkylene groups having from 1 to 12 carbon atoms or polyoxyalkylene groups represented by $(R^dO)_p$, where $R^d$ is H or has from 1 to 12 carbon atoms;

p is any integer from 1 to 50; each $(R^dO)$ moiety may be the same or different; $R^b$ is —N($R^e$)—, where $R^e$ is H, an alkyl group having from 1 to 12 carbon atoms, or X—Y, where X is as defined below or $R^5$, and Y is a carboxylic acid, phosphate, sulfate, sulfonate, or tertiary ammonium group); and a, b, c, and d are numbers in ranges so that $1.0 \leq a+b \leq 2.5$, $0.001 \leq c \leq 1.5$, and $0.001 \leq d \leq 1.5$.}

[2] The co-modified organopolysiloxane according to [1], wherein Q is a group containing a saccharide component obtained by a reaction between an amino group and a hydroxy functional saccharide.

[3] The co-modified organopolysiloxane according to [1] or [2], wherein Q is a sugar lactone amide alkyl group obtained by a reaction between a silicon-bonded amino group represented by:
—$R^{12}$—(N($R^{13}$)—$R^{14}$)$_w$—$NR^{15}R^{16}$ (wherein $R^{12}$ is an alkylene group having from 2 to 8 carbon atoms;
$R^{13}$, $R^{15}$, and $R^{16}$ are hydrogen atoms or monovalent organic groups having from 1 to 10 carbon atoms, but at least one of all of $R^{13}$, $R^{15}$, and $R^{16}$ is a hydrogen atom; and
$R^{14}$ is an alkylene group having from 1 to 4 carbon atoms; and w is a number in a range of $0 \leq w \leq 6$) and
a sugar lactone compound.

[4] The co-modified organopolysiloxane according to one of [1] to [3] represented by the following structural formula (1-1).

[Formula 4]

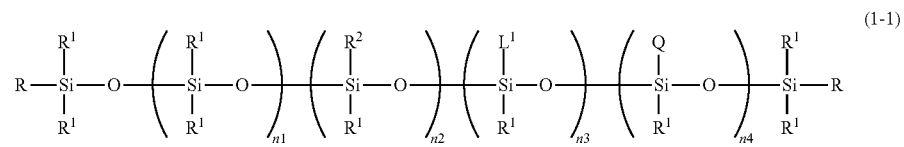

(1-1)

{In this formula, $R^1$, $R^2$, $L^1$ and Q are groups synonymous with the groups described above, and R is a group selected from $R^1$, $R^2$, $L^1$, and Q; however, when n3=0, at least one R is $L^1$; and when n4=0, at least one R is Q; and (n1+n2+n3+n4) is a number in a range from 0 to 50; n1 is a number in a range from 0 to 45, n2 is a number in a range from 0 to 30, n3 is a number in a range from 0 to 20, and n4 is a number in a range from 0 to 2.}

[5] The co-modified organopolysiloxane according to one of [1] to [4] represented by the following structural formula (1-1-1).

[Formula 5]

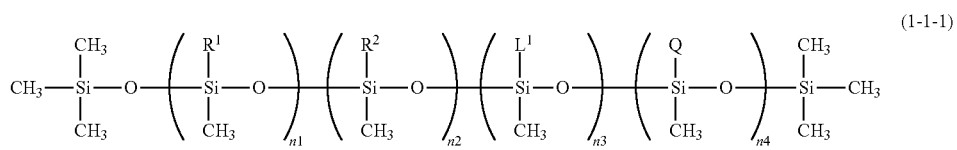

(1-1-1)

{In this formula, $R^1$, $R^2$, $L^1$, and Q are groups synonymous with the groups described above, (n1+n2+n3+n4) is a number in a range from 2 to 50, n1 is a number in a range from 0 to 45, n2 is a number in a range from 0 to 30, n3 is a number in a range from 1 to 20, and n4 is a number in a range from 0.1 to 2.}

[6] The co-modified organopolysiloxane according to [4] or [5], wherein in structural formula (1-1) or structural formula (1-1-1), $L^1$ is a functional group represented by the following general formula (2-1) or general formula (2-2):

General Formula (2-1):

[Formula 6]

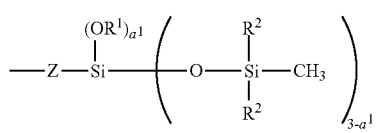

(2-1)

General Formula (2-2):

[Formula 7]

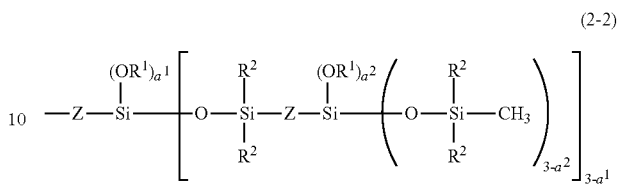

(2-2)

(In these formulae, $R^1$, $R^2$, and Z are synonymous with the groups described above, and $a^1$ and $a^2$ are each independently numbers in a range of 0 to 3); and Q is a sugar lactone amide alkyl group $Q^1$ obtained by a reaction between a silicon-bonded amino group represented by:

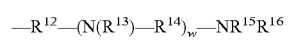

(wherein $R^{12}$ is an alkylene group having from 2 to 8 carbon atoms;

$R^{13}$, $R^{15}$, $R^{16}$ are hydrogen atoms or monovalent organic groups having from 1 to 10 carbon atoms, but at least one of all of $R^{13}$, $R^{15}$, and $R^{16}$ is a hydrogen atom;

$R^{14}$ is an alkylene group having from 1 to 4 carbon atoms; and w is a number in a range of $0 \leq w \leq 6$) and a sugar lactone compound.

[7] The co-modified organopolysiloxane according to [6] represented by the following structural formula (1-1-A) or (1-1-B).

[Formula 8]

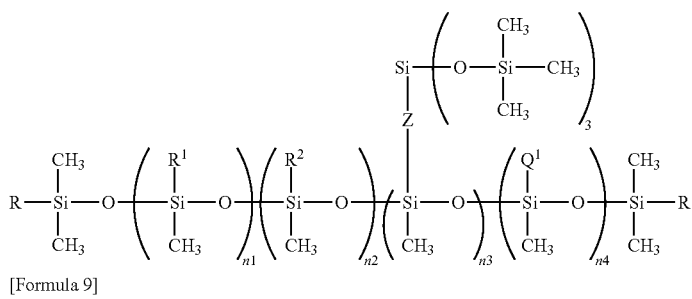

(1-1-A)

[Formula 9]

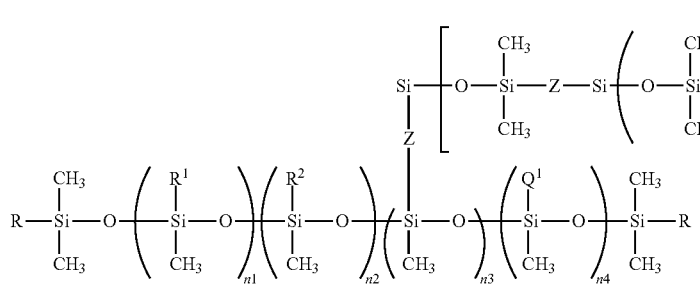

(1-1-B)

{In these formulae, Z, $R^1$, $R^2$, and $Q^1$ are groups synonymous with the groups described above;

R is a group selected from $R^1$, $R^2$, and L and $Q^1$ described above; (n1+n2+n3+n4) is a number in a range from 2 to 50; n1 is a number in a range from 0 to 45, n2 is a number in a range from 0 to 30, n3 is a number in a range from 1 to 20, and n4 is a number in a range from 0.1 to 2.}

[8] A method for producing the co-modified organopolysiloxane according to one of [1] to [7], the method comprising the following steps (I) to (III).

Step (I): a step of producing a co-modified organopolysiloxane intermediate having a functional group that can react with a compound having a saccharide component directly or after a deprotection reaction by co-hydrosilylating: a compound having a siloxane dendron structure;

a compound having a functional group that can react with a compound having a saccharide component directly or after a deprotection reaction; and an organohydrogenpolysiloxane.

Step (II): a step of producing a co-modified organopolysiloxane intermediate having a functional group that can react with a compound having a saccharide component by performing a deprotection reaction as necessary on the co-modified organopolysiloxane intermediate obtained in step (I).

Step (III): a step of reacting the co-modified organopolysiloxane intermediate obtained in step (I) or step (II) and a compound having a saccharide component.

[9] The method for producing a co-modified organopolysiloxane according to [8], wherein step (II) is an essential step; and the compound having a functional group that can react with a compound having a saccharide component after a deprotection reaction is an allylamine protected by an organosilyl group.

[10] The method for producing a co-modified organopolysiloxane according to [9], wherein the organosilyl group is a bis-dimethylsilylethylene group.

[10-1] The method for producing a co-modified organopolysiloxane according to one of [8] to [10], most preferably comprising the following steps (I) to (III).

Step (I-A): a step of producing a co-modified organopolysiloxane intermediate having a functional group that can react with a compound having a saccharide component after a deprotection reaction by co-hydrosilylating: a compound having a siloxane dendron structure; an allylamine protected by a bis-dimethylsilylethylene group; and an organohydrogenpolysiloxane.

Step (II-B): a step of producing a co-modified organopolysiloxane intermediate having a functional group that can react with a compound having a saccharide component by performing a deprotection reaction on the co-modified organopolysiloxane intermediate obtained in step (I).

Step (III): a step of reacting the co-modified organopolysiloxane intermediate obtained in step (I) or step (II) and a compound having a saccharide component.

[11] A surface treatment agent comprising the co-modified organopolysiloxane according to one of [1] to [7].

[12] A powder treatment agent comprising the co-modified organopolysiloxane according to one of [1] to [7].

[13] A powder composition comprising: (A) the co-modified organopolysiloxane according to one of [1] to [7]; and (B) a powder or coloring agent.

[14] The powder composition described in [13], wherein the component (B) is one or two or more selected from the group consisting of an inorganic pigment powder, an organic pigment powder, and a resin powder, having an average diameter in a range of 1 nm to 20 μm.

[15] A powder-in-oil dispersion comprising: (A) the co-modified organopolysiloxane according to one of [1] to [7]; (B) a powder or coloring agent; and (C) one or more oil agents selected from a silicone oil, a nonpolar organic compound, or a low-polarity organic compound that is a liquid at 5 to 100° C.

[16] A preparation for external use comprising the co-modified organopolysiloxane according to one of [1] to [7].

[17] The preparation for external use described in [16] that is a cosmetic composition or a medicament.
[18] A cosmetic composition comprising the powder composition according to [13] or [14].
[19] A cosmetic composition comprising the powder-in-oil dispersion according to [15].
[20] A makeup cosmetic comprising: (A) the co-modified organopolysiloxane according to one of [1] to [7]; (B) a powder or coloring agent; and (C) a silicone oil, a nonpolar organic compound, or a low-polarity organic compound that is a liquid from 5 to 100° C."

Advantageous Effects of Invention

With the present invention, a novel co-modified organopolysiloxane copolymer which is less expensive than polyglycerine or xylitol-modified organopolysiloxane, has better production efficiency of a powder dispersion in a mixed oil agent system than conventional polyether-modified organopolysiloxane, powder dispersibility, and compatibility with a wide range of cosmetic raw materials, and can be advantageously used as a cosmetic raw material can be advantageously provided on an industrial scale, in particular. As a result, preparation of particularly a powder-in-oil dispersion is facilitated and, moreover, a product characterized by having superior powder dispersibility and stability can be provided. Additionally, according to the present invention, a powder treatment agent comprising the organopolysiloxane, a powder that is surface treated using the powder treatment agent, a powder composition comprising the co-modified organopolysiloxane copolymer, and a powder-in-oil dispersion comprising an oil agent; and, moreover a preparation for external use, particularly a make-up cosmetic composition can be provided. A variety of cosmetic compositions comprising the novel co-modified organopolysiloxane of the present invention can be provided. However, of these, a cosmetic composition using the powder-in-oil dispersion described above, particularly a make-up cosmetic composition can be advantageously provided.

DETAILED DESCRIPTION OF THE INVENTION

Hereinafter, a novel co-modified organopolysiloxane of the present invention, uses thereof as various types of treatment agents, and in particular, uses as a powder treatment agent and as a cosmetic raw material will be described in detail. Additionally, detailed descriptions of a powder-in-oil dispersion, an external use preparation, advantageously a cosmetic composition, and particularly advantageously a make-up cosmetic composition using the novel co-modified organopolysiloxane of the present invention will be given.

It is possible to apply the novel co-modified organopolysiloxane according to the present invention to uses held in common with the co-modified organopolysiloxane recited in Patent Document 5 (WO/2011/049248). That is, particularly in terms of the dosage form, type, and formulation examples of the cosmetic composition, the novel co-modified organopolysiloxane according to the present invention can be used as various treatment agents, particularly as a powder treatment agent and a cosmetic raw material; can be used in combination with an optional cosmetic raw material component; and can be used as an external use preparation, in the same manner as the co-modified organopolysiloxane recited in Patent Document 5.

The co-modified organopolysiloxane according to the present invention is a co-modified organopolysiloxane having a group that has a siloxane dendron structure and a sugar or sugar derivative residue as a hydrophilic group, and more specifically is a co-modified organopolysiloxane represented by the following general formula (1). (Hereinafter, the group represented by $L^1$ in general formula (1), which is a silylalkyl group expressed by the following general formula (2) when i=1, is also referred to as the "carbosiloxane dendrimer" and the "silylalkyl group having a siloxane dendron structure". Similarly, the group (Q) containing a saccharide component is also expressed as a "sugar or sugar derivative residue") General Formula (1):

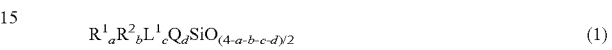

$$R^1_a R^2_b L^1_c Q_d SiO_{(4-a-b-c-d)/2} \quad (1)$$

In general formula (1),
$R^1$ is a substituted or unsubstituted monovalent hydrocarbon group having from 1 to 30 carbon atoms, or a hydrogen atom;
$R^2$ is a substituted or unsubstituted straight-chain or branched monovalent hydrocarbon group having from 6 to 30 carbon atoms, or a chainlike organosiloxane group represented by the following general formula (2-1);

[Formula 10]

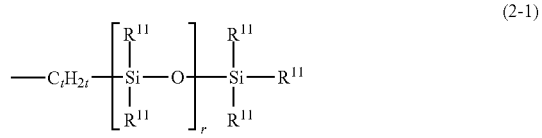

(2-1)

(wherein $R^{11}$ is a substituted or unsubstituted monovalent hydrocarbon group having from 1 to 30 carbon atoms, a hydroxyl group, or a hydrogen atom,
at least one of the $R^{11}$ moieties being the monovalent hydrocarbon group; t is a number in a range of 2 to 10; and r is a number in a range of 1 to 500); or the following general formula (2-2):

[Formula 11]

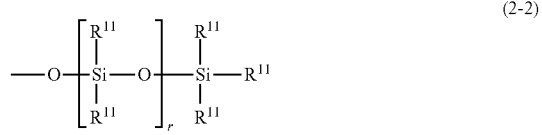

(2-2)

(wherein $R^{11}$ and r are as described above);
$L^1$ represents a silylalkyl group having the siloxane dendron structure expressed by the following general formula (3) when i=1;

[Formula 12]

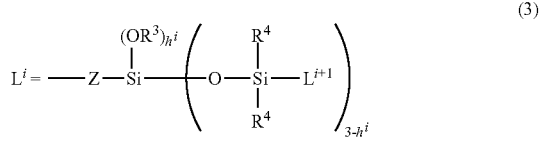

(3)

(wherein
R$^3$ represents a substituted or unsubstituted, straight or branched monovalent hydrocarbon group having from 1 to 30 carbon atoms; R$^4$ each independently represents an alkyl group having 1 to 6 carbon atoms or phenyl group; Z represents a divalent organic group; i represents a generation of the aforementioned silylalkyl group represented by L$^i$ and is an integer of 1 to k when k is a number of generations that is a number of repetitions of the silylalkyl group; the number of generations k is an integer from 1 to 10; L$^{i+1}$ is the silylalkyl group when i is less than k, and R$^4$ when i=k, and h$^i$ is a number in a range from 0 to 3);

Q is a group containing a saccharide component having the formula X-(G$^1$)$_n$-(G$^2$)$_m$, wherein G$^1$ in the formula is a saccharide component having from 5 to 12 carbon atoms; n+m is from 1 to 10; and n or m may be 0, G$^2$ is a saccharide component having from 5 to 12 carbon atoms which may be additionally substituted with an organic or organic silicon group;

X is a linking group independently selected from a group consisting of the following:
—R$^5$—NHC(O)—R$^6$—;
—R$^5$—NHC(O)O—R$^6$—;
—R$^5$—NH—C(O)—NH—R$^6$—;
—R$^6$—O—R$^6$—;
—R$^5$—CH(OH)—CH$_2$—O—R$^6$—;
—R$^6$—S—R$^6$—;
—R$^5$—CH(OH)—CH$_2$—NH—R$^6$—; and
—R$^6$—N(R$^1$)—R$^6$— wherein R$^5$ and R$^6$ are divalent spacer groups containing (R$^a$)$_u$, (R$^b$)$_v$, and (R$^c$)$_x$, where at least one of u, v, and x must be 1; R$^7$ and R$^9$ are alkylene groups having from 1 to 12 carbon atoms or polyoxyalkylene groups represented by (R$^d$O)$_p$, where R$^d$ is H or has from 1 to 12 carbon atoms;

p is any integer from 1 to 50; each (R$^d$O) moiety may be the same or different; R$^b$ is —N(R$^e$)—, where R$^e$ is H, an alkyl group having from 1 to 12 carbon atoms, or X—Y, where X is as defined below or R$^5$, and Y is a carboxylic acid, phosphate, sulfate, sulfonate, or tertiary ammonium group); and a, b, c, and d are numbers in ranges so that 1.0≤a+b≤2.5, 0.001≤c≤1.5, and 0.001≤d≤1.5.

In general formula (1), R$^1$ is a substituted or unsubstituted monovalent hydrocarbon group having from 1 to 30 carbon atoms, or a hydrogen atom. However, the monovalent organic group R$^1$ does not comprise a group corresponding with the L$^1$ or Q moieties described above and, particularly independently represents an aryl group or an alkyl group having from 1 to 10 carbon atoms. Examples thereof include methyl, ethyl, n-propyl, i-propyl, n-butyl, i-butyl, s-butyl, pentyl, neopentyl, cyclopentyl, hexyl, and similar straight, branched, or annular alkyl groups; and a phenyl groups. From an industrial point of view, R$^1$ preferably is a methyl group or a phenyl groups. Additionally, R$^1$ may be a group wherein the hydrogen atoms bonded to the carbon atoms of these groups are substituted at least partially by fluorine or a similar halogen atom, or by an organic group having an epoxy group, an acyl group, a carboxyl group, an amino group, a (meth)acryl group, a mercapto group, or the like.

R$^2$ is a functional group that is comprised optionally in the co-modified organopolysiloxane according to the present invention and is a substituted or unsubstituted, straight or branched monovalent hydrocarbon group having from 6 to 30 carbon atoms. Particularly, in cases where all of the R$^1$ moieties are alkyl groups having not more than 5 carbon atoms (particularly methyl groups) or are phenyl groups, it is preferable that the long chain hydrocarbon group R$^2$ be comprised for the purpose of improving affinity with, particularly, hydrocarbon-based oil agents (i.e. cosmetic raw materials). Preferable examples of the R$^2$ moiety include hexyl groups, heptyl groups, octyl groups, decyl groups, dodecyl groups, and similar alkyl groups having not less than 6 carbon atoms; cyclohexyl groups and similar cycloalkyl groups; tolyl groups, xylyl groups, naphthyl groups, and similar aryl groups; and groups wherein the hydrogen atoms bonded to the carbon atoms of these groups are substituted at least partially by fluorine or a similar halogen atom, or an organic group having an epoxy group, an acyl group, a carboxyl group, an amino group, a (meth)acryl group, a mercapto group, or the like. The R$^2$ moiety is preferably an alkyl group having from 8 to 20 carbon atoms.

The chain organosiloxane group in general formula (2-1) or (2-2) has a straight chain polysiloxane chain structure, unlike a silylalkyl group, which has a siloxane dendron structure. In general formula (2-1) or (2-2), R$^{11}$ are each independently a substituted or unsubstituted monovalent hydrocarbon group having from 1 to 30 carbon atoms, a hydroxyl group, or a hydrogen atom. The substituted or unsubstituted monovalent hydrocarbon group having from 1 to 30 carbon atoms is an alkyl group having from 1 to 30 carbon atoms, an aryl group having from 6 to 30 carbon atoms, an aralkyl group having from 6 to 30 carbon atoms, or a cycloalkyl group having from 6 to 30 carbon atoms, and is exemplified by a methyl group, ethyl group, propyl group, butyl group, pentyl group, hexyl group, heptyl group, octyl group, decyl group, or other alkyl group; a cyclopentyl group, cyclohexyl group, or other cycloalkyl group; or a phenyl group, tolyl group, or other aryl group. The hydrogen atoms bonded to the carbon atoms of these groups may be substituted at least partially by fluorine or a similar halogen atom, or an organic group containing an epoxy group, acyl group, carboxyl group, amino group, methacryl group, mercapto group, or the like. A methyl group, a phenyl group, or a hydroxyl group is particularly preferable as R$^{11}$. A configuration in which a part of R$^{11}$ is a methyl group and another part of R$^{11}$ is a long chain alkyl group having from 8 to 30 carbon atoms is also preferable.

In general formula (2-1) or (2-2), t is a number in a range from 2 to 10; r is a number in a range from 1 to 500; and r preferably is a number in a range from 2 to 500. Such a straight chain organosiloxane group is hydrophobic. From the standpoint of compatibility with various oil agents, r preferably is a number in a range from 1 to 100, and particularly preferably is a number in a range from 2 to 30.

Examples of the substituted or unsubstituted, straight or branched monovalent hydrocarbon group having from 1 to 30 carbon atoms (the R$^3$ moieties in general formula (3)) include methyl groups, ethyl groups, propyl groups, butyl groups, pentyl groups, hexyl groups, heptyl groups, octyl groups, and similar alkyl groups; cyclopentyl groups, cyclohexyl groups, and similar cycloalkyl groups; vinyl groups, allyl groups, butenyl groups, and similar alkenyl groups; phenyl groups, tolyl groups, and similar aryl groups; benzyl groups and similar aralkyl groups; and groups wherein the hydrogen atoms bonded to the carbon atoms of these groups are substituted at least partially by fluorine or a similar halogen atom, or an organic group containing an epoxy group, a glycidyl group, an acyl group, a carboxyl group, an amino group, a methacryl group, a mercapto group, or the like (provided that the total number of carbon atoms is from 1 to 30).

In the co-modified organopolysiloxane according to the present invention, a group (-$L^1$) having a siloxane dendron structure and a modified group other than the group (-Q) containing a saccharide component—in particular, a short-chain or medium-chain hydrocarbon-based group—may be introduced or designed as $R^1$ for the purpose of providing further functionality. Specifically, when $R^1$ is a substituted monovalent hydrocarbon group, a substituent can be preferably selected in accordance with desired characteristics and uses. For example, when using the co-modified organopolysiloxane as a cosmetic composition raw material, it is possible to introduce an amino group, aminoethyl aminopropyl group, carboxyl group, or the like as the substituted group of a monovalent hydrocarbon group, for the purpose of improving the sensation during use, feeling to touch, persistence, and the like.

Particularly, the $R^1$ moieties are preferably monovalent hydrocarbon groups having from 1 to 8 carbon atoms and that are free of unsaturated aliphatic bonds or monovalent fluorinated hydrocarbon groups. Examples of the monovalent hydrocarbon groups not having unsaturated aliphatic bonds belonging to the $R^3$ moiety include methyl groups, ethyl groups, propyl groups, butyl groups, pentyl groups, hexyl groups, and similar alkyl groups; phenyl groups, tolyl groups, xylyl groups, and similar aryl groups; and aralkyl groups such as benzyl groups. Examples of the monovalent fluorinated hydrocarbon group include trifluoropropyl groups, pentafluoroethyl groups, and similar perfluoroalkyl groups. From an industrial perspective, $R^3$ is preferably a methyl group, an ethyl group, or a phenyl group, and more preferably from 90 mol to 100% of all the $R^1$ moieties are selected from methyl groups, ethyl groups, or phenyl groups.

In general formula (1), the group represented by $L^1$ is a silylalkyl group having a siloxane dendron structure, and is defined as the silylalkyl group expressed by general formula (3) when i=1. The silylalkyl group having a siloxane dendron structure includes a structure in which a carbosiloxane unit is extended in the form of a dendrimer and is thus a functional group that exhibits high water repellency in comparison to a linear or simply branched polysiloxane unit. The co-modified organopolysiloxane of the present invention can exhibit high compatibility with not only silicone oils, but also various oil agents such as hydrocarbon oils and ester oils due to the presence of a siloxane dendron structure. The co-modified organopolysiloxane of the present invention can also exhibit a unique and excellent feel of use due to the presence of a siloxane dendron structure. In addition, due to a well-balanced combination with hydrophilic groups, the co-modified organopolysiloxane of the present invention can be provided with an excellent oil agent thickening effect and gelling performance. Further, the silylalkyl group having a siloxane dendron structure is chemically stable, and for this reason, the silylalkyl group is a functional group providing advantageous characteristics such as usability in combination with a wide range of cosmetic composition components.

In general formula (3), $R^4$ is a phenyl group or an alkyl group having from 1 to 6 carbon atoms. Examples of the alkyl group having from 1 to 6 carbon atoms include methyl, ethyl, n-propyl, i-propyl, n-butyl, i-butyl, s-butyl, pentyl, neopentyl, cyclopentyl, hexyl, and similar straight, branched, or cyclic alkyl groups.

In general formula (3), i represents a generation of the silylalkyl group represented by $L^i$, and is an integer of 1 to k when k is a number of generations, which is a number of repetitions of the silylalkyl group. The number of generations k is an integer from 1 to 10, and $L^{i+1}$ is the silylalkyl group when i is less than k and is a methyl group or a phenyl group when i=k. In particular, R4 is preferably a methyl group when i=k. In addition, h' is a number in a range of 0 to 3.

From an industrial standpoint, the number of generations k is preferably an integer from 1 to 3, and more preferably is 1 or 2. In each of the number of generations, the group represented by $L^1$ is expressed as follows. In the formula, $R^2$ and Z are groups synonymous with the groups described above.

When the number of generations is k=1, $L^1$ is expressed by the following general formula (3-1):

[Formula 13]

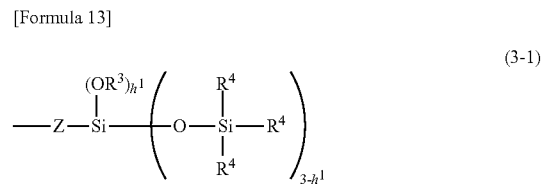

(3-1)

When the number of generations is k=2, $L^1$ is expressed by the following general formula (3-2):

[Formula 14]

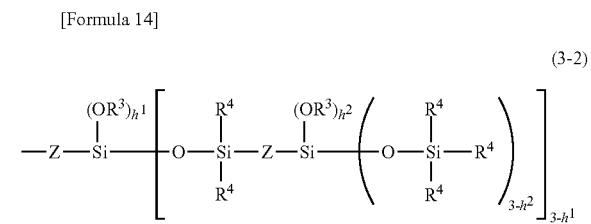

(3-2)

When the number of generations is k=3, $L^1$ is expressed by the following general formula (3-3):

[Formula 15]

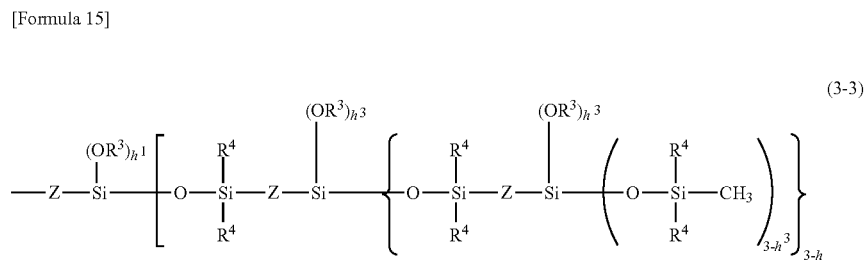

(3-3)

In general formula (3), in the structures expressed by the general formulae (3-1) to (3-3) in which $h^i$ are each independently a number in a range from 0 to 3 and the number of generations is from 1 to 3, $h^1$, $h^2$, and $h^3$ are each independently a number in a range from 0 to 3. These $h^i$ moieties are preferably a number in a range from 0 to 1, and h' is, in particular, preferably 0.

In general formulae (3) and (3-1) to (3-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not restricted to the functional groups described above. Preferably, Z are each independently a group selected from divalent organic groups expressed by the following general formula.

[Formula 16]

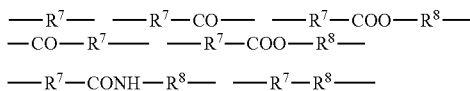

In the general formula described above, $R^7$ each independently represents a substituted or unsubstituted, straight or branched chain alkylene group or alkenylene group having from 2 to 22 carbon atoms or an arylene group having from 6 to 22 carbon atoms. More specifically, examples of $R^5$ include an ethylene group, a propylene group, a butylene group, a hexylene group, and similar straight alkylene groups; a methylmethylene group, a methylethylene group, a 1-methylpentylene group, a 1,4-dimethylbutylene group, and similar branched alkylene groups. $R^5$ is preferably a group selected from an ethylene group, a propylene group, a methylethylene group, and a hexylene group.

In the general formula described above, $R^8$ is a group selected from divalent organic groups expressed by the following formulae:

[Formula 17]

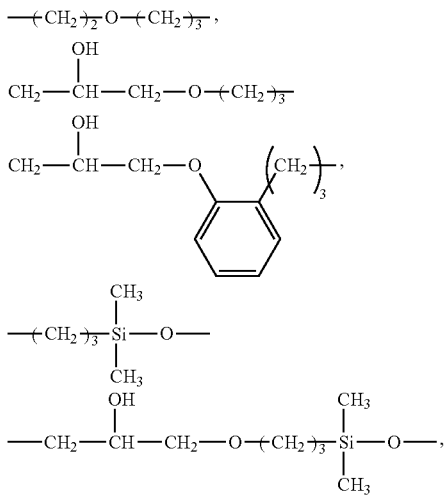

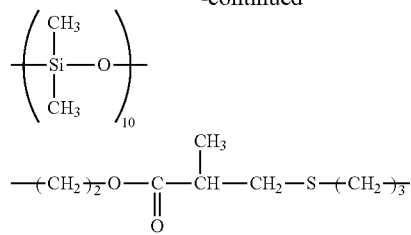

In particular, Z in $L^1$ is preferably a divalent organic group expressed by general formula $-R^7-$ introduced by a reaction between a silicon-bonded hydrogen atom and an alkenyl group. Similarly, Z is preferably a divalent organic group expressed by general formula $-R^7-COO-R^8-$ introduced by a reaction between a silicon-bonded hydrogen atom and an unsaturated carboxylic acid ester group. On the other hand, in the silylalkyl group represented by $L^i$, in which the number of generations k is 2 or more, and $L^i$ is $L^2$ to $L^k$, Z is preferably an alkylene group having from 2 to 10 carbon atoms and, in particular, is preferably a group selected from an ethylene group, a propylene group, a methylethylene group, and a hexylene group, and most preferably is an ethylene group.

Saccharide functional silicones and methods for producing the same are known in this technical field. For example, U.S. Pat. No. 4,591,652 describes a method of producing a polyhydroxysilane by reacting a silane having an amine terminal substituent with an aldonolactone. Japanese Patent No. 62-68820 discloses an organopolysiloxane containing a saccharide residue created from an aminosiloxane and a saccharide lactone. WO/94/29324 describes a siloxanyl-modified compound containing an epoxy trisiloxane reaction product and a surfactant or a surface improving agent formed from a saccharide lactone. WO/02/088456 describes an amide-functional aminopolydiorganosiloxane formed from an aminosiloxane and a saccharide lactone.

Synthesis methods for linking saccharides and siloxanes are also known in this technical field. For example, U.S. Pat. No. 5,831,080 describes an organosilicone compound containing a glycoside group created by means of the hydrosilylation of an allyl functional saccharide group. U.S. Pat. No. 6,517,933B1 describes a hybrid polymer material comprising a set of natural building blocks including saccharides and a set of synthetic building blocks including polysiloxanes. Many possible linking methods are described. All of the disclosures of the reference patent documents described above are incorporated into this specification by reference. Further, saccharide siloxanes can be modified by means of a reaction with an anionic or cationic monomer at the functional site of a sugar siloxane.

In the present invention, Q is a group containing a saccharide component having the formula $X-(G^1)_n-(G^2)_m$. It is particularly preferable for Q to be a sugar lactone amide alkyl group formed by an amide bond between a sugar lactone compound and an aminoalkyl group, but Q is not limited to this example.

In the formula, $G^1$ is a saccharide component having from 5 to 12 carbon atoms; b+c is from 1 to 10; and when b or c is 0, $G^2$ is a saccharide component having from 5 to 12 carbon atoms which may be additionally substituted with an organic or organic silicon group. Here, the saccharide component is preferably a sugar residue structure derived from a hydroxy functional saccharide and is even more preferably a structure originating from aldonic acid, oligoaldonic acid, uronic acid, oligouronic acid, or a sugar residue derived therefrom. In the present invention, a structure originating from a sugar residue derived from a sugar lactone compound (formed by the cyclodehydration of saccharic acid in the molecule) is particularly preferable. By having such a structure, the group containing a saccharide component represented by Q can provide the co-modified organopolysiloxane of the present invention with hydrophilicity.

Examples of sugar lactone compounds in which saccharic acid is subjected to intramolecular cyclization include lactones originating from aldonic acid, uronic acid, lactobionic acid, or the like. More specific examples include lactones of aldonic acids derived from reducing monosaccharides such as D-glucose, D-galactose, D-allose, D-aldose, D-mannose, D-gulose, D-idose, and D-talose; lactones of aldonic acids derived from reducing disaccharides such as maltose, cellobiose, lactose, xylobiose, isomaltose, nigerose, and kojibiose; lactones of aldonic acids derived from reducing trisaccharides such as maltotriose, panose, and isomaltotriose; lactones of aldonic acids derived from reducing oligosaccharides of four or more sugars; lactones of uronic acids such as D-glucuronic acid, L-iduronic acid, and mannuronic acid; and lactones of lactobionic acids. In addition, these may be used alone or as a mixture in the reaction. Aldonolactones derived from D-glucose such as gluconolactone (GL) and lactobionolactones (LBL) derived from lactobionic acid are particularly preferable.

In addition, in the formula, X is a linking group independently selected from a group consisting of the following:
—$R^5$—NHC(O)—$R^6$—;
—$R^5$—NHC(O)O—$R^6$—;
—$R^5$—NH—C(O)—NH—$R^6$—;
—$R^5$—O—$R^6$—;
—$R^5$—CH(OH)—$CH_2$—O—$R^6$—;
—$R^5$—S—$R^6$—;
—$R^5$—CH(OH)—$CH_2$—NH—$R^6$—; and
—$R^5$—N($R^1$)—$R^6$—
wherein $R^5$ and $R^6$ are divalent spacer groups containing $(R^a)_u$, $(R^b)_v$, and $(R^c)_x$, where at least one of u, v, and x must be 1; $R^a$ and $R^c$ are alkylene groups having from 1 to 12 carbon atoms or polyoxyalkylene groups represented by $(R^dO)_p$, where $R^d$ is H or has from 1 to 12 carbon atoms; p is any integer from 1 to 50; each $(R^dO)$ moiety may be the same or different; $R^b$ is —N($R^e$)—, where $R^e$ is H, an alkyl group having from 1 to 12 carbon atoms, or X—Y, where X is as defined below or $R^5$, and Y is a carboxylic acid, phosphate, sulfate, sulfonate, or tertiary ammonium group.

X is specifically a divalent functional group containing an amide, amino, urethane, urea, ester, ether, thioether, or acetal functional linking group and is preferably a linking group containing an amide bond obtained by a reaction between an amino group and a hydroxy functional saccharide.

In particular, X is preferably an amide functional linking group obtained by a reaction between a silicon-bonded aminoalkyl group and a sugar lactone compound. That is, the co-modified organopolysiloxane of the present invention particularly preferably has a sugar lactone amide alkyl group obtained by a reaction between a silicon-bonded aminoalkyl group silicon atom and a sugar lactone compound as the group (Q) containing a saccharide component.

More specifically, in the present invention, Q is particularly preferably a sugar lactone amide alkyl group ($Q^1$) obtained by a reaction between a silicon-bonded amino group represented by:

—$R^{12}$—(N($R^{13}$)—$R^{14}$)$_w$—N$R^{15}R^{16}$ (wherein $R^{12}$ is an alkylene group having from 2 to 8 carbon atoms;
$R^{13}$, $R^{15}$, and $R^{16}$ are hydrogen atoms or monovalent organic groups having from 1 to 10 carbon atoms, but at least one of all of $R^{13}$, $R^{15}$, and $R^{16}$ is a hydrogen atom;
$R^{14}$ is an alkylene group having from 1 to 4 carbon atoms; and w is a number in a range of 0≤w≤6) and
a sugar lactone compound. At this time, the amino group is preferably an aminoalkyl group having from 2 to 20 carbon atoms and is particularly preferably an aminopropyl group or an amino ethylamino isobutyl group. In addition, the sugar lactone compound is preferably an aldonolactone or the like and is particularly preferably gluconolactone (GL) or lactobionolactone (LBL). Here, the reaction between the aminoalkyl group and the sugar lactone compound is preferably achieved by mixing the sugar lactone compound in an amount of from 1.0 to 1.3 times the molar amount of a co-modified organopolysiloxane intermediate having an aminoalkyl group in a solvent and then stirring for 3 to 20 hours under heat reflux at a solution concentration of from 5 to 30 wt. %. Lower alcohols such as methanol, ethanol, 1-propanol, and 2-propanol are suitable as the solvent used at this time.

Preferable examples of the co-modified organopolysiloxane according to the present application include a straight co-modified organopolysiloxane represented by structural formula (1-1) below.

[Formula 18]

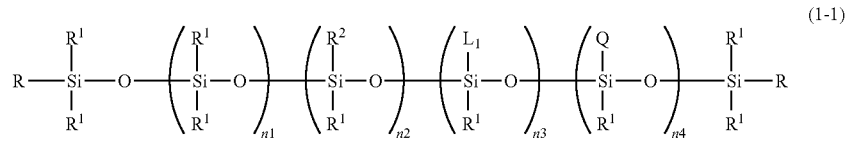

(1-1)

In this formula, $R^1$, $R^2$, $L^1$ and Q are groups synonymous with the groups described above, and R is a group selected from $R^1$, $R^2$, $L^1$, and Q. However, when n3=0, at least one R is $L^1$;
and when n4=0, at least one R is Q.

In the straight-chain co-modified organopolysiloxane represented by the structural formula (1-1), (n1+n2+n3+n4) is a number in a range from 0 to 50, preferably from 5 to 45, and particularly preferably from 10 to 40.

n1 is a number in a range of 0 to 45, preferably from 5 to 45, and more preferably from 10 to 45.

n2 is a number in a range of 0 to 30, preferably from 0 to 25, and more preferably from 0 to 20.

n3 is a number in a range of 0 to 20, preferably from 1 to 15, and more preferably from 1 to 10.

n4 is a number in a range of 0 to 2, preferably from 0.1 to 1.8, and more preferably from 0.2 to 1.5. When n1 to n4 are within the ranges described above, the co-modified organopolysiloxane of the present application has a comparatively low molecular weight and can be oriented on the surface of various powders so as to impart an appropriate degree of water repellency. Therefore, the co-modified organopolysiloxane can be very suitably used as a powder surface treatment agent used in the surface treatment or dispersion of a cosmetic powder, in particular.

An industrially preferable example of the co-modified organopolysiloxane of the present application is a straight-chain co-modified organopolysiloxane represented by the following structural formula (1-1-1).

[Formula 19]

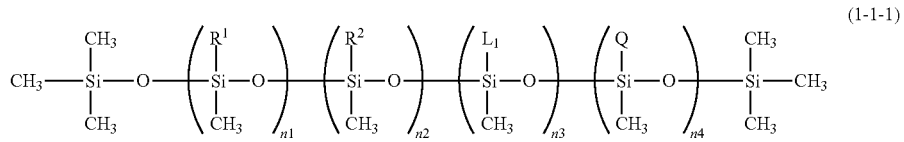

(1-1-1)

In this formula, $R^1$, $R^2$, $L^1$, and Q are groups synonymous with the groups described above, and n1 to n4 are numbers synonymous with the numbers described above.

Preferable examples of the co-modified organopolysiloxane according to the present application include co-modified organopolysiloxanes represented by the following structural formulae (1-1-A) and (1-1-B).

[Formula 20]

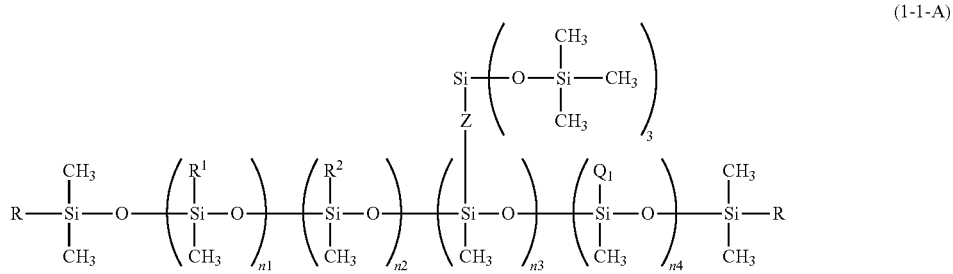

(1-1-A)

[Formula 21]

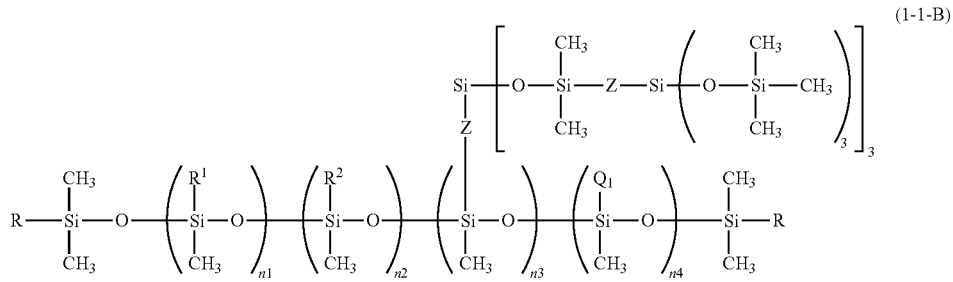

(1-1-B)

In structural formula (1-1-A) or (1-1-B), Z, $R^1$, $R^2$, and $Q^1$ are groups synonymous with those described above; and R is a group selected from the aforementioned $R^1$, $R^2$, $L^1$, and $Q^1$. In addition, n1 to n4 are numbers synonymous with those described above.

The co-modified organopolysiloxane according to the present application can be obtained by, in a first step, performing an addition reaction on a compound having a siloxane dendron structure having one carbon-carbon double bond at one terminal of the molecular chain and a compound having a reactive functional group such as an alkenyl group at one terminal of the molecular chain and having a functional group that can react with a compound having a saccharide component directly or after a deprotection reaction at the other terminal with respect to an organohydrogenpolysiloxane having a reactive functional group such as Si—H so as to produce a reactive organopolysiloxane intermediate; and in a third step following an optional second step of performing a deprotection reaction, reacting the reactive organopolysiloxane intermediate with a compound having a saccharide component. The type of addition reaction in the first step is not particularly limited, but from the standpoint of reaction control, purity, and yield, the addition reaction is preferably performed in the presence of a hydrosilylation reaction catalyst. In addition, the crude product of the co-modified organopolysiloxane obtained as a result of this two-stage reaction may be a mixture with the compound having a saccharide component.

In particular, in order to obtain the co-modified organopolysiloxane of the present invention with high purity and high yield by means of a hydrosilylation reaction, the compound having a functional group that can react with the compound having a saccharide component is preferably a compound having a reactive functional group such as an alkenyl group at one terminal of the molecular chain and having an amino group protected by an organic group at the other terminal. The compound having such a protected amino group can be selected as desired but is, from an industrial standpoint, particularly preferably an allylamine in which the amino group is protected by an organic group such as an organosilyl group, an amide group, or an imide group.

Examples of the protecting group of the allylamine described above include 1,2-bis-dimethylsilylethylene, 1,2-bis-dimethylsilylbenzene, trimethylsilyl groups, succinic anhydride, phthalic anhydride, dialkylmaleic anhydride, and benzoyl chloride, and 1,2-bis-dimethylsilyletylene is particularly effective from the perspective of operability and ease of deprotection.

The co-modified organopolysiloxane according to the present application can be most preferably obtained by, in the first step, performing co-hydrosilylation on a compound having a siloxane dendron structure having one carbon-carbon double bond at one terminal of the molecular chain and an allylamine protected by a bis-dimethylsilylethylene group with respect to an organohydrogenpolysiloxane having a reactive functional group such as Si—H so as to produce a co-modified organopolysiloxane intermediate;

in the second step, performing a deprotection reaction on the amino group of the co-modified organopolysiloxane intermediate; and in the third step, reacting the reactive organopolysiloxane intermediate following the deprotection reaction with a compound having a saccharide component (in particular, a sugar lactone compound).

Applications of the Co-Modified Organopolysiloxane

The novel co-modified organopolysiloxane according to the present invention (hereinafter, referred to as "component (A)") is hydrophobic, has a silylalkyl group having a siloxane dendron structure exhibiting high water repellency and a group having a hydrophilic saccharide component in the same molecule, and has excellent compounding stability with oleophilic raw materials. Therefore, the novel co-modified organopolysiloxane according to the present invention is useful as various types of treatment agents and cosmetic raw material components and is extremely useful, in particular, as a surface treatment agent for use in a cosmetic and particularly as a powder treatment agent for use in the surface treatment of a powder or the dispersion of a powder. In particular, in the applications described above, it is preferable for the degree of polymerization of the co-modified organopolysiloxane to be relatively low and for the modification rate by the silylalkyl group having a siloxane dendron structure and the group containing a saccharide compound to be within a certain range. Therefore, most preferable are co-modified organopolysiloxanes having chainlike structures represented by the above structural formulae (1-1), (1-1-1), (1-1-A), and (1-1-B), in particular.

Use as a Powder Treatment Agent

The co-modified organopolysiloxane according to the present invention has integrated hydrophilic groups, which can be strongly oriented on the surface of various powders so as to impart an appropriate degree of water repellency. Therefore, the co-modified organopolysiloxane according to the present invention can be suitably used as a powder surface treatment agent for the purpose of surface-treating or dispersing a cosmetic powder.

Particularly, when used as a powder treatment agent, dispersion stability in a mixed oil agent system of the co-modified organopolysiloxane according to the present invention is superior compared to conventional co-modified organopolysiloxanes. Thus, a powder-in-oil dispersion having superior stability in which the powder does not agglomerate or precipitate after preparing a powder composition obtained by treating the powder surface using a treatment agent can be provided, even when a method is used where the powder composition is dispersed in an oil agent dispersing medium and even when the powder is one where conventional powder treatment agents result in difficulties in stable dispersion.

The co-modified organopolysiloxane of the present invention has excellent compatibility with various other hydrophilic and hydrophobic components in the cosmetic composition, and can enhance the dispersibility and stability of a powder in a cosmetic composition that comprises a powder. Thus, the powder treatment agent of the present invention and the powder surface treatment agent of the present invention can improve the stability of a cosmetic composition that comprises a powder and can improve the uniform dispersibility of this powder. A cosmetic composition that comprises a powder that is surface treated using the powder surface treatment agent has high stability and this powder uniformly disperses in this cosmetic composition.

A compounded amount of the co-modified organopolysiloxane in the powder treatment agent of the present invention is not particularly limited provided that powder treatment effects are displayed and, for example, can be from 50 to 100 wt. % (mass %), and is preferably from 70 to 100 wt. %, and more preferably from 90 to 100 wt. %.

The powder treatment agent of the present invention may comprise a combination of the co-modified organopolysiloxane according to the present invention and another known surface treatment agent and be used to surface treat a powder. Examples of the other surface treatment agent include surface treatment agents based on methylhydrogenpolysiloxane, silicone resin, metal soap, silane coupling agents, silica, alumina, titanium oxide, and similar inorganic oxides; perfluoroalkylsilane, perfluoroalkyl phosphate ester salts, and similar fluorine compounds. Thus, the powder surface treatment agent of the present invention may, for example, comprise from 0.1 to 50 wt. % of the other surface treatment agent and preferably comprises from 1 to 30 wt. % and more preferably comprises from 5 to 10 wt. % of the other surface treatment agent.

When using the co-modified organopolysiloxane according to the present invention as the powder surface treatment agent, a compounded amount of the co-modified organopolysiloxane and the powder or coloring agent is preferably in a range from 0.1 to 50 parts by mass, and more preferably from 0.5 to 40 parts by mass per 100 parts by mass of the powder or coloring agent. If the compounded amount is less than the lower limit described above, effects by the surface treating may be insufficient. On the other hand, even if the compounded amount exceeds the upper limit described above, greater prominent changes in texture will not occur, and the tendency for the powder and the co-modified organopolysiloxane to form a uniform mixture will increase.

The co-modified organopolysiloxane according to the present invention can be used to treat a powder surface using a conventional method. This method is not particularly limited and, for example, can be appropriately selected from the methods described below.

1. A method in which the target powder is surface treated by being dispersed in a medium selected from organic solvents in which the treatment agent has been compounded.
2. A method in which the powder is surface treated by mixing the powder and the powder treatment agent and, thereafter, crushing the mixture in a pulverizer such as a ball mill, a jet mill, or the like.
3. A treatment method in which the treatment agent is compounded in a solvent, the powder is dispersed in the mixture so as to adhere the treatment agent to the surface of the powder, and then the powder is dried and sintered.

Powder Composition

Additionally, the present invention relates to a powder composition comprising (A) the co-modified organopolysiloxane according to the present invention and (B) a powder or coloring agent. The powder composition can be obtained, according to the methods described above or the like, by mixing (B) the powder or coloring agent and (A) the co-modified organopolysiloxane according to the present invention, regardless of the purpose (i.e. to surface treat the powder, improve dispersibility of the powder, to act as a premix for a cosmetic raw material, or the like).

Powder-in-Oil Dispersion

Additionally, "powder-in-oil dispersion" as used in the present invention, refers to a product in which a powder composition obtained as described above is dispersed in an oil agent or, alternatively, a product in which a co-modified organopolysiloxane is dissolved or dispersed in an oil agent, and then the powder is added by being mixed and dispersed therein; and a form thereof is that of a liquid dispersed product. This liquid dispersed product is also called a "slurry".

The oil agent is not particularly limited provided that a liquid dispersion can be prepared, and is an oil agent that is commonly used as a component of a cosmetic composition. Furthermore, while the oil agent is typically liquid at room temperature, it may be solid such as a wax, and may also be in a highly viscous (high viscosity) gum-like state or paste-like state. The oil agent is preferably one or more selected from (C) a silicone oil, a nonpolar organic compound, and a low polarity organic compound that are liquid from 5 to 100° C.

The powder-in-oil dispersion of the present invention can be appropriately prepared according to a known method such as the methods described below.
1. A method in which the powder composition obtained as described above is added to and dispersed in ester oil, silicone oil, or a similar oil agent.
2. A method in which the co-modified organopolysiloxane is dissolved or dispersed in the oil agent described above, the powder is added thereto, and the mixture is blended using a ball mill, a bead mill, a sand mill, or a similar disperser.

The obtained powder-in-oil dispersion can be compounded as-is in a preparation for external use (particularly in a cosmetic composition).

The powder composition and the powder-in-oil dispersion comprising the co-modified organopolysiloxane according to the present invention can be suitably used as a preparation for external use, particularly for a cosmetic composition or a cosmetic raw material.

(B) Powder or Coloring Agent

The powder or coloring agent (B) used in the powder composition, the powder-in-oil dispersion, and the like according to the present invention is a component that is commonly used in a cosmetic composition and includes white and colored pigments as well as extender pigments. The white and colored pigments are used to impart color and the like to the cosmetic composition, and the extender pigments are used to improve the tactile sensation and the like of the cosmetic composition. In the present invention, white and colored pigments as well as extender pigments commonly used in cosmetic compositions can be used as the powder without any particular restriction. In the present invention, preferably, one or two or more of the powders are compounded. The form (sphere, bar, needle, plate, amorphous, spindle, cocoon, or the like), particle size (aerosol, micro-particle, pigment-grade particle, or the like), and particle structure (porous, nonporous, or the like) of the powder are not limited in any way, but an average primary particle size is preferably in a range of 1 nm to 100 μm. Particularly, when compounding the powder or coloring agent as a pigment, preferably one or two or more selected from an inorganic pigment powder, an organic pigment powder, and a resin powder having an average diameter in a range from 1 nm to 20 μm is compounded.

Examples of the powder include inorganic powders, organic powders, surfactant metal salt powders (metallic soaps), colored pigments, pearl pigments, metal powder pigments, and the like. Compounded products of these pigments can be used. Furthermore, the surfaces of these pigments may be water-repellent treated.

Specific examples include the same powders or colorants recited in paragraphs 0150 to 0152 of Patent Document 5 (WO/2011/049248, filed by the present applicant).

The powders or coloring agents described above are preferably treated using other powder dispersants or surface treatment agents. In particular, the powders or coloring agents may be dispersed or surface-treated by the novel powder treatment agents and treatment methods proposed by the inventors of the invention of the present application in WO/2009/022621, Japanese Unexamined Patent Application Publication No. 2011-148784, Japanese Unexamined Patent Application Publication No. 2011-149017, Japanese Unexamined Patent Application Publication No. 2011-246704, Japanese Unexamined Patent Application Publication No. 2011-246705, Japanese Unexamined Patent Application Publication No. 2011-246706, WO/2009/022621, WO/2011/049246, WO/2011/049248, Japanese Patent Application 2011-286973, and the like, or treated to form a slurry using these novel powder treatment agents and the aforementioned oil agents. These novel treatment agents have an excellent improving effect on the unique texture and performance such as dispersion stability, so improving effects on the functionality, texture, storage stability, and the like of the cosmetic can be anticipated when used in combination with the novel cosmetic raw material of the present invention.

Of the powders recited, description of a silicone elastomer powder shall be given. The silicone elastomer powder is a crosslinked product of a straight diorganopolysiloxane formed principally from diorganosiloxy units (D units), and can be preferably obtained by crosslinking an organohydrogenpolysiloxane having a silicon-bonded hydrogen atom on the sidechain or the molecular terminal and a diorganopolysiloxane having an unsaturated hydrocarbon group such as an alkenyl group or the like on the sidechain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented. In addition, by carrying out surface treatment using the co-modified organopolysiloxane, it is possible to impart a moist feeling to touch without reducing the suede-like feeling to touch of a silicone elastomer powder. Furthermore, when blending the co-modified organopolysiloxane in addition to a silicone elastomer powder in a cosmetic composition, it is possible to improve the dispersion stability of the powder in the overall cosmetic composition and obtain a cosmetic composition that is stable over time.

The silicone elastomer powder can be in various forms such as spherical, flat, amorphous, or the like. The silicone elastomer powder may also be in the form of an oil dispersion. With the cosmetic composition of the present invention, the silicone elastomer powder is particulate in form, and the primary particle size observed using an electron microscope and/or the average primary particle size measured by laser analysis or scattering is in a range from 0.1 to 50 μm. Additionally, a silicone elastomer powder having spherical primary particles can be preferably compounded. The silicone elastomer that constitutes the silicone elastomer powder is preferably one having a hardness, as measured using a type A durometer in the "Rubber, Vulcanized or Thermoplastic—Determination of Hardness" specified in JIS K 6253, of 80 or lower, and more preferably 65 or lower.

Of these silicone elastomer powders, specific examples of silicone elastomer spherical powders are the same as those disclosed by the applicants in paragraph [0168] of the above-mentioned Patent Document 5 (WO/2011/049248), and may be a silicone elastomer powder that has been subjected to a variety of water-repellent treatments, as disclosed in paragraphs [0150] to [0152].

The mixture of the co-modified organopolysiloxane (A) and the powder or coloring agent (B) is a form in which the powder is dispersed in the co-modified organopolysiloxane, and a compounded amount of the powder in the mixture is not particularly limited but is preferably in a range from 50 to 99 wt. % and more preferably in a range from 80 to 90 wt. % of the entire mixture.

(C) Oil Agent

The oil agent used in the powder-in-oil dispersion and the like according to the present invention preferably is one or more oil agent selected from a silicone oil, a nonpolar organic compound, and a low polarity organic compound that are liquid from 5 to 100° C. A hydrocarbon oil and a fatty acid ester oil are preferable as the nonpolar organic compound and the low polarity organic compound. These are components that are particularly widely used as base materials for make-up cosmetic compositions, but it is possible to additionally use one or more type of compound selected from among publicly known vegetable oils and fats, animal oils and fats, higher alcohols, liquid fatty acid triglycerides, artificial sebum, and fluorine-based oils as well as these oil agents. The co-modified organopolysiloxane also displays superior dispersibility in these non-silicone-based oil agents and, therefore the hydrocarbon oil and the fatty acid ester oil can be stably compounded in a cosmetic composition and moisturizing characteristics imparted by these non-silicone-based oil agents can be maintained. Thus, the co-modified organopolysiloxane can improve stability over time of these non-silicone-based oil agent in a cosmetic composition.

By combining the hydrocarbon oil and/or the fatty acid ester oil with the silicone oil, in addition to the dry tactile sensation unique to silicone oils, moisture will be retained on the skin and a moisturizing feel whereby the skin or hair feels moisturized (also referred to as a luxurious tactile sensation) and smooth tactile sensation can be imparted to the cosmetic composition of the present invention. Moreover, there is a benefit in that stability over time of the cosmetic composition will not be negatively affected. Furthermore, with a cosmetic composition comprising the hydrocarbon oil and/or the fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non silicone-based oil agent (e.g. a hydrocarbon oil, a fatty acid ester oil, or the like), the cosmetic composition comprising a non silicone-based oil agent along with a silicone oil is advantageous in that a smoother, more luxurious tactile sensation is imparted.

These oil agents are the same as those disclosed by the applicants in paragraphs [0130] to [0135] and [0206] and so on in the above-mentioned Patent Document 5 (WO/2011/049248). Examples of the fluorine-based oil include perfluoropolyether, perfluorodecalin, perfluorooctane, and the like.

A compounded amount of the oil agent in the powder-in-oil dispersion of the present invention is not particularly limited but is preferably in a range from 0.1 to 50 wt. % and more preferably in a range from 0.5 to 25 wt. % in the raw material for use in cosmetic compositions.

The co-modified organopolysiloxane and the powder composition or the powder-in-oil dispersion comprising the co-modified organopolysiloxane can be suitably used as a preparation for external use, particularly for a cosmetic composition or a cosmetic raw material. Such preparations for external use, particularly cosmetic compositions or medicaments are within the scope of the present invention.

Particularly, the co-modified organopolysiloxane and the powder composition or the powder-in-oil dispersion comprising the co-modified organopolysiloxane can be advantageously used as a make-up cosmetic composition raw material. Such make-up cosmetic compositions comprising the co-modified organopolysiloxane and the powder composition or the powder-in-oil dispersion comprising the co-modified organopolysiloxane particularly are within the scope of the preferable embodiments of the present invention.

Water (D) can be further compounded in the cosmetic composition of the present invention and, thereby, the cosmetic composition of the present invention may take the form of an oil-in-water emulsion or a water-in-oil emulsion. In this case, the cosmetic composition of the present invention displays superior emulsion stability and sensation during use. The preparation of a hydrous cosmetic composition or emulsion cosmetic composition is the same as that disclosed by the applicants in paragraphs [0128] to [0146] in the above-mentioned Patent Document 5 (WO/2011/049248).

A uniformly soluble product (emulsion premix) that is the cosmetic raw material is formed by mixing the co-modified organopolysiloxane with the powder and the oil agent optionally in the presence of ethanol or a similar alcohol. The premix is mixed with water using the device described above. Thus, a cosmetic composition in the form of a uniform oil-in-water emulsion or water-in-oil emulsion can be produced.

The cosmetic composition of the present invention can further comprise (E) other surfactants. These other surfactants are components that function as cleansing components of the skin or the hair or, alternatively, as the oil agent or an emulsifier, and can be selected as desired depending on the type and function of the cosmetic composition. More specifically, the other surfactants can be selected from the group consisting of an anionic surfactant, a cationic surfactant, a nonionic surfactant, an amphoteric surfactant, and a semipolar surfactant. Preferably a silicone-based nonionic surfactant is used in combination.

These surfactants are the same as those disclosed by the applicants in paragraphs [0162], [0163] and [0195] to [0201] and so on in the above-mentioned Patent Document 5 (WO/2011/049248). The co-modified organopolysiloxane used in the present invention has a hydrophilic moiety and a hydrophobic moiety in the molecule and, therefore, has functionality as a dispersing agent. Thus, in cases where used in combination with a silicone-based nonionic surfactant, the component (E) functions as an aid to enhance the stability of the nonionic surfactant and may improve overall stability of the formulation. Particularly, the co-modified organopolysiloxane is preferably used in combination with polyoxyalkylene-modified silicones, polyglyceryl-modified silicones, glyceryl-modified silicones, and sugar alcohol-modified silicones. Moreover, the silicone-based nonionic surfactants described above in which an alkyl branch, a straight chain silicone branch, a siloxane dendrimer branch, or the like is (as desired) provided with the hydrophilic group can be advantageously used.

Depending on the purpose thereof, the cosmetic composition of the present invention can comprise one or two or more polyhydric alcohols and/or lower monohydric alcohols as a component (F). These alcohols are the same as those disclosed by the applicants in paragraphs [0159] and [0160] and so on in the above-mentioned Patent Document 5 (WO/2011/049248).

Depending on the purpose thereof, the cosmetic composition of the present invention can comprise one or two or more inorganic salts and/or organic salts as a component (G). These salts are the same as those disclosed by the applicants in paragraph [0161] and so on in the above-mentioned Patent Document 5 (WO/2011/049248).

Depending on the purpose thereof, the cosmetic composition of the present invention can include at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax as a component (H). These silicone components are the same as those disclosed by the applicants in paragraphs [0161] to [0193] and so on in the above-mentioned Patent Document 5 (WO/2011/049248). Examples of the component (H) other than those recited in Patent Document 5 include (H-1): a silicone polyester elastomer gel described in WO/2007/109240 and WO/2009/006091 in which compatibility with various components is enhanced and stable thickening effects are displayed as a result of introducing a polyoxypropylene group. Examples of commercially available products thereof include Dow Corning EL-8050 ID SILICONE ORGANIC ELASTOMER BLEND, Dow Corning EL-8051 IN SILICONE ORGANIC ELASTOMER BLEND, Dow Corning EL-7040 HYDRO ELASTOMER BLEND; and (H-2): PITUITOUS SILICONE FLUIDS described in WO/2011/028765 and WO/2011/028770. At least one type selected from these products can be used depending on the purpose of the cosmetic composition of the present invention. Furthermore, the liquid and slightly-crosslinkable organopolysiloxane proposed in Japanese Patent Application No. 2010-289722 and the domestic priority claimed therefrom (filed by the present applicant) can be used in the present invention.

The cosmetic composition of the present invention can, depending on the purpose of the cosmetic composition, comprise one or two or more water-soluble polymers as a component (J). These water-soluble polymers are the same as those disclosed by the applicants in paragraphs and so on in the above-mentioned Patent Document 5 (WO/2011/049248).

Depending on the purpose thereof, the cosmetic composition of the present invention can include one or two or more ultraviolet light blocking components as a component (K). These ultraviolet light blocking components are the same as the organic and inorganic ultraviolet light blocking components disclosed by the applicants in paragraphs [0202] to [0204] and so on in the above-mentioned Patent Document 5 (WO/2011/049248). The ultraviolet light blocking components that can be used particularly preferably include at least one type selected from among the group comprising fine particulate titanium oxide, fine particulate zinc oxide, paramethoxy cinnamic acid 2-ethylhexyl, 4-tert-butyl-4'-methoxydibenzoylmethane, diethylamino hydroxybenzoyl hexyl benzoate, benzotriazole-based ultraviolet radiation absorbers, and triazine-based ultraviolet radiation absorbers such as 2,4,6-tris[4-(2-ethylhexyloxycarbonyl)anilino]1,3,5-triazine {INCI: octyl triazone}, 2,4-bis{[4-(2-ethyl-hexyloxy)-2-hydroxy]phenyl}-6-(4-methoxyphenyl)-1,3,5-triazine {(INCI: bis-ethylhexyloxyphenol methoxyphenyltriazine (product name: Tinosorb S™)}. These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

In the cosmetic composition of the present invention, by using the raw material for use in cosmetic compositions comprising the co-modified organopolysiloxane and the ultraviolet light blocking component together, the ultraviolet light blocking component can be stably dispersed in the cosmetic composition and the tactile sensation and the storage stability of the entire cosmetic composition can be improved. Therefore, superior UV blocking capacity can be imparted to the cosmetic composition.

In the cosmetic composition of the present invention, a total compounded amount of the ultraviolet light blocking component with respect to the entire cosmetic composition is in a range from 0.1 to 40.0 wt. % (mass %), and more preferably in a range from 0.5 to 15.0 wt. % (mass %).

Various components other than the components described above can be used in the cosmetic composition of the present invention, provided that such use does not impair the effects of the present invention. Examples thereof include oil-soluble gelling agents, organo-modified clay minerals, preservatives, bioactive components, skin beautifying components, pH adjusting agents, antioxidants, solvents, chelating agents, moisturizing components, perfumes, and the like. These optional cosmetic product components are the same as those disclosed by the applicants in paragraphs [0207], [0208] and [0220] to [0228] and so on in the above-mentioned Patent Document 5 (WO/2011/049248).

Additionally, in cases where the cosmetic composition according to the present invention is an anti-perspirant, or depending on the purpose of the cosmetic composition, the cosmetic composition can contain an anti-perspiration active component and/or a deodorant agent. These anti-perspiration components and deodorant components are the same as those disclosed by the applicants in paragraphs [0209] to [0219] and so on in the above-mentioned Patent Document 5 (WO/2011/049248). Similarly, in cases in which the cosmetic composition according to the present invention is an anti-perspirant composition, the preparation and method of use of the various anti-perspirant compositions are the same as those disclosed by the applicants in paragraphs [0234] to [0275] and so on of the above-mentioned Patent Document 5 (WO/2011/049248).

The external use preparation according to the present invention is not particularly limited, provided that it is a composition for application to the human body as a cosmetic composition or a medicament. Specific examples of cosmetic composition products of the present invention include skin cleansing agent products, skin care products, makeup products, anti-perspirant products, ultraviolet light blocking products, and similar skin use cosmetic products; hair use cleansing agent products, hair dressing products, hair use coloration products, hair growth products, hair rinsing products, hair conditioning products, hair treatment products, and similar hair use cosmetic products; and bath use cosmetic products. Examples of the medicament of the present invention include hair regrowth agents, hair growth promoters, analgesics, germicides, anti-inflammatory agents, refreshing agents, and skin anti-aging agents, but are not limited thereto.

The types, forms, and containers of the preparation for external use according to the present invention are the same as those recited in paragraphs [0230] to [0233] and the like of Patent Document 5 (WO/2011/049248, filed by the present applicant), but the co-modified organopolysiloxane is particularly useful as a raw material for various make-up cosmetic compositions. Additionally, the cosmetic composition according to the present invention is most advantageous as a make-up cosmetic composition comprising the co-modified organopolysiloxane (A), the powder or colorant (B), and the silicone oil, nonpolar organic compound, or low polarity organic compound (C) that is liquid from 5 to 100° C.

Specific examples of the make-up cosmetic composition include; foundations, liquid foundations, oil-based foundations, makeup bases, powders, face powders, lipsticks, lip creams, muddy colored lipsticks or rouges, lip glosses, eye shadows, eye liners, eye creams, eyebrow pencils, eyelash cosmetic products, eyebrow pencils, eyebrow blushes, mascaras, blushers, cheek cosmetics (cheek color, cheek rouge), manicures, pedicures, nail colors, nail laquers, enamel removers, nail polishes, and similar makeup products.

EXAMPLES

Hereinafter, the present invention is described in detail with reference to Practical Examples and Comparative Examples, but it should be understood that the present invention is not limited to these Practical Examples. The viscosity (dynamic viscosity) values are measured at 25° C. In the following compositional formulas, Me$_3$SiO groups (or Me$_3$Si group) are notated as "M", Me$_2$SiO groups are notated as "D", and MeHSiO groups are notated as "D$^H$". Units in which a methyl group in D is modified by any substituent is notated as D$^R$.

Synthesis Examples

Synthesis of Allylamine A Protected by Bis-Dimethylsilylethylene

First, 85.7 g of allylamine, 379.4 g of triethylamine, and 650 g of toluene were prepared, and 323.0 g of bis-dimethylchlorosilylethylene (33% toluene solution) was dripped into the solution while stirring at room temperature. When the solution was then aged for three hours at 90° C. and cooled to room temperature, the precipitation of hydrochloride was observed. After the organic layer was washed with saturated saline, the toluene layer was distilled so as to obtain 213 g of a protected allylamine A. In the working examples and the like below, this allylamine protected by bis-dimethylsilylethylene is called "allylamine A".

Working Example 1

Synthesis of Co-Modified Organopolysiloxane Compound P1

First, 32.4 g of tris-trimethylsiloxyvinylsilane and 6.3 g of allylamine A were charged into 61.3 g of a methylhydrogenpolysiloxane represented by the average composition formula MD$_{15}$D$^H_3$M in a stepwise manner in a reaction vessel in the presence of 0.1 g of a platinum catalyst, and a reaction was performed for ten hours at 75 to 90° C. while stirring under a stream of nitrogen. After the completion of the reaction was confirmed by an alkali decomposition gas generation method (i.e., the remaining Si—H groups are decomposed using a KOH ethanol/water solution, and the reaction rate is calculated from the volume of the produced hydrogen gas), 30 g of isopropanol (IPA) was added and heated at 90° C. to deprotect the amino groups. When the low-boiling-point matter was distilled out at 150° C. after the completion of the deprotection of amino groups was confirmed by an amino % measurement (titration of amino residues using hydrochloric acid), 90 g of an intermediate represented by MD$_{15}$D$^{R1}_{2.4}$D$^{RA}_{0.6}$M was obtained. Next, 30 g of the obtained intermediate was reacted for two hours at 70° C. with 2.2 g of gluconolactone in 30 g of IPA. After the disappearance of amino groups was confirmed by an amino % measurement, the low-boiling-point matter was distilled out at 110° C., and when the substance was then filtered, 32.5 g of a novel co-modified organopolysiloxane having a siloxane dendron structure represented by the average composition formula MD$_{15}$D$^{R1}_{2.4}$D$^{R2}_{0.6}$M and a group containing a saccharide component derived from gluconolactone (sugar residue) was obtained.

In the formula, R$^1$ and R$^A$ are the structures indicated below, and R$^2$ is a gluconolactone amide propyl group obtained by a reaction between an aminopropyl group and gluconolactone.

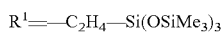

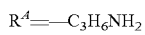

Working Example 2

Synthesis of Co-Modified Organopolysiloxane Compound P2

First, 18.5 g of tris-trimethylsiloxyvinylsilane and 6.3 g of allylamine A were charged into 80 g of a methylhydrogenpolysiloxane represented by the average composition formula MD$_{33}$D$^H_3$M in a stepwise manner in a reaction vessel in the presence of 0.1 g of a platinum catalyst, and a reaction was performed for ten hours at 75 to 90° C. while stirring under a stream of nitrogen. After the completion of the reaction was confirmed by an alkali decomposition gas generation method (i.e., the remaining Si—H groups are decomposed using a KOH ethanol/water solution, and the reaction rate is calculated from the volume of the produced hydrogen gas), 20 g of isopropanol (IPA) was added and heated at 90° C. to deprotect the amino groups. When the low-boiling-point matter was distilled out at 150° C. after the completion of the deprotection of amino groups was confirmed by an amino % measurement (titration of amino residues using hydrochloric acid), 97.2 g of an intermediate represented by $MD_{33}D^{R1}{}_2D^{RA}{}_1M$ was obtained. Next, 30 g of the obtained intermediate was reacted for three hours at 80° C. with 1.5 g of gluconolactone in 40 g of IPA. After the disappearance of amino groups was confirmed by an amino % measurement, the low-boiling-point matter was distilled out at 110° C., and when the substance was then filtered, 24.2 g of a novel co-modified organopolysiloxane having a siloxane dendron structure represented by the average composition formula $MD_{33}D^{R1}{}_2D^{R2}{}_1M$ and a group containing a saccharide component derived from gluconolactone (sugar residue) was obtained.

In the formula, $R^1$ and $R^A$ are the structures indicated below, and $R^2$ is a gluconolactone amide propyl group obtained by a reaction between an aminopropyl group and gluconolactone.

$R^1 = —C_2H_4—Si(OSiMe_3)_3$ $R^A = —C_3H_6NH_2$

Working Example 3

Synthesis of Co-Modified Organopolysiloxane Compound P3

First, 25.2 g of tris-trimethylsiloxyvinylsilane, 5.7 g of allylamine A, and 17.5 g of 1-dodecene were charged into 51.6 g of a methylhydrogenpolysiloxane represented by the average composition formula $MD_{19}D^H{}_8M$ in a stepwise manner in a reaction vessel in the presence of 0.05 g of a platinum catalyst, and a reaction was performed for ten hours at 75 to 90° C. while stirring under a stream of nitrogen. After the completion of the reaction was confirmed by an alkali decomposition gas generation method (i.e., the remaining Si—H groups are decomposed using a KOH ethanol/water solution, and the reaction rate is calculated from the volume of the produced hydrogen gas), 30 g of methanol and 30 g of isopropanol (IPA) were added and heated at 90° C. to deprotect the amino groups. When the low-boiling-point matter was distilled out at 150° C. after the completion of the deprotection of amino groups was confirmed by an amino % measurement (titration of amino residues using hydrochloric acid), 86.4 g of an intermediate represented by $MD_{19}D^{R1}{}_3D^{RA}{}_1D^{R3}{}_4M$ was obtained.

Next, 43 g of the obtained intermediate was reacted for seven hours at 90° C. with 1.9 g of gluconolactone in 40 g of IPA. After the disappearance of amino groups was confirmed by an amino % measurement, the low-boiling-point matter was distilled out at 110° C., and when the substance was then filtered, 41 g of a novel co-modified organopolysiloxane having a siloxane dendron structure represented by the average composition formula $MD_{19}D^{R1}{}_3D^{R2}{}_1D^{R3}{}_4M$ and a group containing a saccharide component derived from gluconolactone (sugar residue) was obtained.

In the formula, $R^1$, $R^A$, and $R^3$ are the structures indicated below, and $R^2$ is a gluconolactone amide propyl group obtained by a reaction between an aminopropyl group and gluconolactone.

$R^1 = —C_2H_4—Si(OSiMe_3)_3$ $R^A = —C_3H_6NH_2$ $R^3 = —C_{12}H_{25}$

Synthesis of Organopolysiloxane Compound R1

First, 50 g of an amino-modified silicone represented by the average composition formula $MD_{350}D^{RA}{}_4M$ was reacted at 90° C. with 1.5 g of gluconolactone in 50 g of IPA in a reaction vessel. When the low-boiling-point matter was distilled out at 110° C. after the completion of the deprotection of amino groups was confirmed by an amino % measurement (titration of amino residues using hydrochloric acid), 47.7 g of an organopolysiloxane having a group containing a saccharide component derived from gluconolactone represented by the average composition formula $MD_{350}D^{R2}{}_4M$ (sugar residue) was obtained.

In the formula, $R^A$ is the structure indicated below, and $R^2$ is a gluconolactone amide propyl group obtained by a reaction between an aminopropyl group and gluconolactone.

$R^A = —C_3H_6NH_2$

Organopolysiloxane Compound R2

The organopolysiloxane compound R2 used in the comparative examples was the following product.

ES5612: Polyether-modified silicone (product name: ES5612, manufactured by Dow Corning Toray Co., Ltd.)

The average composition formulae of the "co-modified organopolysiloxane compounds P1" to "P3" of the present invention and the "co-modified organopolysiloxane compound R1 for comparison" of the comparative examples, which were synthesized with the methods described above, are collectively shown in Table 1.

TABLE 1

| Co-modified organopolysiloxane | Average composition formula |
|---|---|
| P1 | $MD_{15}D^{R1}{}_{2.4}D^{R2}{}_{0.6}M$ |
| P2 | $MD_{33}D^{R1}{}_2D^{R2}{}_1M$ |
| P3 | $MD_{19}D^{R1}{}_3D^{R2}{}_1D^{R3}{}_4M$ |
| Organopolysiloxane for comparison | |
| R1 | $MD_{350}D^{R2}{}_4M$ |

In the table, the structures and types of the functional groups are as follows.
$R^1 = —C_2H_4—Si(OSiMe_3)_3$
$R^2 =$ gluconolactone amide propyl group obtained by a reaction between an aminopropyl group and gluconolactone
$R^3 = —C_{12}H_{25}$

[Evaluation of Dispersion Stability]

Slurry-like microparticle dispersions were prepared according to the formulations and preparation methods shown in Dispersion Preparation 1 to Dispersion Preparation 5 below. These microparticle dispersions were then evaluated from the standpoints of dispersion characteristics and change in viscosity with time. 1,000 mPas was set as the standard for the viscosity of the slurries and those that had viscosities that were lower than 1,000 mPas were considered to be "low viscosity" and those that were higher than 1,000 mPas were considered to be "high viscosity". Additionally, in cases where the slurry gelified after agitating using a paint shaker in the stage of producing the slurry, the product was labeled "slurry production impossible". The results are shown in Table 2. The components used in the preparation of each dispersion are as follows.

(1) Micro-Particle Powder: Fine Particulate Titanium Oxide
   Product name: MT-01 (manufactured by Tayca Corporation)
   Particle size: 10 nm
(2) Dispersing Medium: Decamethyl Cyclopentasiloxane
   Product name: DC245 (manufactured by Dow Corning Toray Co., Ltd.)

Working Example

Preparation of Dispersion 1

First, 20 g of fine particulate titanium oxide, 5 g of the co-modified organopolysiloxane (P1) of Working Example 1, and 25 g of decamethylcyclopentasiloxane were mixed, and 200 g of zirconia beads (0.8 mm D) were added and mixed for 15 hours with a paint shaker (made by Asada Iron Works, Co., Ltd.) to form a slurry-like dispersion (TP1).

Working Example

Preparation of Dispersion 2

A slurry-like dispersion (TP2) was produced the same as in the preparation of dispersion 1, except that the co-modified organopolysiloxane (P2) of Practical Example 2 was used in place of the co-modified organopolysiloxane (P1) of Practical Example 1.

Practical Example

Preparation of Dispersion 3

A slurry-like dispersion (TP3) was produced the same as in the preparation of dispersion 1, except that the co-modified organopolysiloxane (P3) of Practical Example 3 was used in place of the co-modified organopolysiloxane (P1) of Practical Example 1.

Comparative Example

Preparation of Dispersion 4

A slurry-like dispersion (TR1) was produced the same as in the preparation of dispersion 1, except that the co-modified organopolysiloxane (R1) of Comparative Example 1 was used in place of the co-modified organopolysiloxane (P1) of Practical Example 1.

Comparative Example

Preparation of Dispersion 5

A slurry-like dispersion (TR2) was produced the same as in the preparation of dispersion 1, except that the co-modified organopolysiloxane (R2) of Comparative Example 2 was used in place of the co-modified organopolysiloxane (P1) of Practical Example 1.

TABLE 2

| Sample | | Titanium oxide slurry | Evaluation |
|---|---|---|---|
| Examples | P1 | TP1 | ∘∘ |
| | P2 | TP2 | Δ∘ |
| | P3 | TP3 | ∘∘ |
| Comparative Examples | R1 | TR1 | x— |
| | R2 | TR2 | ∘x |

Evaluation standards are as follows.
∘∘: Low viscosity slurry producible, no increase in viscosity with time
∘x: Low viscosity slurry producible, gelling with time
Δ∘: High viscosity slurry producible, reduction in viscosity with time
x—: Slurry production impossible As shown in Table 2, with the novel co-modified organopolysiloxanes P1 to P3 according to the present invention, slurries in the form of powder-in-oil dispersions of fine particulate titanium oxide were producible. In contrast, with the comparative compounds R1 and R2, the substances gelled at the time of production or were produced but with stability-related problems, and marked differences were observed in the performance as a powder treatment agent. This arises from the fact that the products of the present invention demonstrate dispersion performance superior to that of the comparative compounds due to a high steric effect resulting from the siloxane dendron structure. In addition, the sugar residues serving as the hydrophilic groups of the products of the present invention have a plurality of hydroxy groups, which may be why the products have high affinity to powders. That is, with the products of the present invention, it is thought that it was possible to produce good titanium slurries since the molecular structure is controlled to a higher degree than in the comparative products.

FORMULATION EXAMPLES

Hereinafter, working examples are given based on the following specific formulations containing the novel co-modified organopolysiloxanes P1 to P3 according to the present invention, but the cosmetic of the present invention is not limited to the types and compositions described in these formulation examples. Note that in the formulations, "part(s)" refers to parts by weight (mass).

Formulation Example 1: Liquid foundation (W/O type)
Formulation Example 2: Liquid foundation (W/O type)
Formulation Example 3: Liquid foundation (O/W type)
Formulation Example 4: Sunscreen cream (W/O type)
Formulation Example 5: Sunscreen (shaking type)
Formulation Example 6: Base cream
Formulation Example 7: Rouge
Formulation Example 8: Liquid rouge
Formulation Example 9: Lipstick
Formulation Example 10: Eye shadow
Formulation Example 11: Mascara

| Formulation Example 1: Liquid foundation (W/O type) (Components) | |
|---|---|
| 1. Dimethylsiloxane (2 cs) | 30 parts |
| 2. Isotridecyl isononanoate | 3 parts |
| 3. Isotridecyl neopentanoate | 2 parts |
| 4. Polyether-modified silicone (note 1) | 1.5 parts |
| 5. Co-modified organopolysiloxane P2 | 0.5 parts |
| 6. Organo-modified clay mineral (Bentone 38V) | 1.5 parts |
| 7. Octyl methoxycinnamate | 5 parts |
| 8. Silicone-treated titanium oxide | 8.5 parts |
| 9. Silicone-treated red iron oxide | 0.4 parts |
| 10. Silicone-treated yellow iron oxide | 1 part |
| 11. Silicone-treated black iron oxide | 0.1 parts |
| 12. Decamethylcyclopentasiloxane, dimethicone crosspolymer (note 2) | 2 parts |

Formulation Example 1: Liquid foundation (W/O type)
(Components)

| | | |
|---|---|---|
| 13. | 1,3-Butylene glycol | 5 parts |
| 14. | Glycerin | 3 parts |
| 15. | Sodium chloride | 0.5 parts |
| 16. | Preservative | q.s. |
| 17. | Purified water | Remainder |
| 18. | Perfume | q.s. |

(note 1)
ES-5300, manufactured by Dow Corning Toray Co., Ltd. was used.
(note 2)
DC9040 manufactured by Dow Corning Corporation was used.

(Production Method)

Step 1: Agitate and mix components 1, 4, 6, 7, and 12.

Step 2: Components 2, 3, 5, and 8 to 11 were kneaded and mixed using a triple roller.

Step 3: Add the mixture obtained in step 2 to the mixture obtained in step 1 while agitating. Agitate and mix further.

Step 4: Add an aqueous phase in which components 13 to 18 are uniformly dissolved to the mixture obtained in Step 3 and emulsify. Fill a container with the emulsion to obtain the product.

The resulting W/O-type liquid foundation demonstrated excellent emulsion stability when used, excellent water resistance and cosmetic durability, excellent masking of skin imperfections and wrinkles, and excellent spread and adhesiveness.

Formulation Example 2: Liquid foundation (W/O type)
(Components)

| | | |
|---|---|---|
| 1. | Isododecane | 20 parts |
| 2. | Isohexadecane | 10 parts |
| 3. | Isotridecyl isononanoat | 3 parts |
| 4. | Glyceryl tricapryl-caprate | 2 parts |
| 5. | Polyether-modified silicone (note 1) | 1.5 parts |
| 6. | Co-modified organopolysiloxane P3 | 0.5 parts |
| 7. | Organo-modified clay mineral (Bentone 38V) | 1.5 parts |
| 8. | Octyl methoxycinnamate | 5 parts |
| 9. | Octylsilane treated titanium oxide | 8.5 parts |
| 10. | Octylsilane-treated red iron oxide | 0.4 parts |
| 11. | Octylsilane-treated yellow iron oxide | 1 part |
| 12. | Octylsilane treated black iron oxide | 0.1 parts |
| 13. | (Dimethicone/bis-isobutyl PPG/20) crosspolymer (note 2) | 2 parts |
| 14. | Isododecane/(acrylate/polytrimethylsiloxy methacrylate) copolymer(note 3) | 1 part |
| 15. | Trimethylsiloxysilicate | 1 part |
| 16. | 1,3-Butylene glycol | 5 parts |
| 17. | Glycerin | 3 parts |
| 18. | Sodium chloride | 0.5 parts |
| 19. | Preservative | q.s. |
| 20. | Purified water | Remainder |
| 21. | Perfume | q.s. |

(note 1)
ES-5300, manufactured by Dow Corning Toray Co., Ltd. was used.
(note 2)
EL-8051, manufactured by Dow Corning Corporation, was used.
(note 3)
FA-4002ID, manufactured by Dow Corning Toray Co., Ltd. was used.

(Production Method)

Step 1: Components 1, 2, 5, 7, 8, 13, 14, and 15 were mixed while stirring.

Step 2: Components 3, 4, 6, and 9 to 12 were kneaded and mixed using a triple roller.

Step 3: Add the mixture obtained in step 2 to the mixture obtained in step 1 while agitating. Agitate and mix further.

Step 4: Add an aqueous phase in which components 16 to 21 are uniformly dissolved to the mixture obtained in Step 3 and emulsify. Fill a container with the emulsion to obtain the product.

The resulting W/O-type liquid foundation demonstrated excellent emulsion stability when used, excellent water resistance and cosmetic durability, excellent masking of skin imperfections and wrinkles, a light texture, and excellent adhesion.

Formulation Example 3: Liquid foundation (O/W type)
(Components)

| | | |
|---|---|---|
| 1. | Carboxydecyl trisiloxane | 1 part |
| 2. | Polysorbate 80 | 1.2 parts |
| 3. | Sorbitan sesquioleate | 0.2 parts |
| 4. | Glyceryl stearate | 1.5 parts |
| 5. | Behenyl alcohol | 2.5 parts |
| 6. | Cyclopentasiloxane | 8 parts |
| 7. | Dimethicone (6 CS) | 3 parts |
| 8. | Squalane | 3 parts |
| 9. | Isotridecyl isononanoate | 3 parts |
| 10. | Glyceryl tricapryl-caprate | 3 parts |
| 11. | Co-modified organopolysiloxane P3 | 0.2 parts |
| 12. | Silicone-treated titanium oxide | 8.5 parts |
| 13. | Silicone-treated red iron oxide | 0.4 parts |
| 14. | Silicone-treated yellow iron oxide | 1 part |
| 15. | Silicone-treated black iron oxide | 0.1 parts |
| 16. | 1,3-Butylene glycol | 8 parts |
| 17. | Sodium hydroxide aqueous solution (1%) | 15 parts |
| 18. | Carbomer (2%) | 10 parts |
| 19. | Purified water | Remainder |

(Production Method)

Step 1: Agitate and mix components 1 to 6 and 8 to 10.

Step 2: Knead and mix component 7 and 11 to 15 using a three-roller mill.

Step 3: Add the mixture obtained in step 2 to the mixture obtained in step 1 while agitating. Agitate and mix further.

Step 4: Add an aqueous phase in which components 16 to 19 are uniformly dissolved to the mixture obtained in Step 3 and emulsify. Fill a container with the emulsion to obtain the product.

The resulting O/W-type liquid foundation demonstrated excellent emulsion stability when used, excellent water resistance and cosmetic durability, excellent masking of skin imperfections and wrinkles, and excellent spread and adhesiveness.

Formulation Example 4: Sunscreen cream (W/O)
(Components)

| | | |
|---|---|---|
| 1. | Dimethicone (2 cs) | 3.8 parts |
| 2. | Isotridecyl isononanoate | 4 parts |
| 4. | Polyether-modified silicone (note 1) | 2 parts |
| 5. | Octyl para-methoxycinnamate | 5 parts |
| 6. | Diethylamino hydroxybenzoyl hexyl benzoate | 2 parts |
| 7. | Organomodified bentonite | 1.2 parts |
| 8. | Titanium oxide dispersion (40 wt. % titanium oxide) (note 2) | 20 parts |
| 9. | Dimethicone/(acrylate/polytrimethylsiloxy methacrylate) copolymer | 3 parts |
| 10. | 1,3-Butylene glycol | 7 parts |
| 11. | Sodium citrate | 0.2 parts |
| 12. | Sodium chloride | 0.5 parts |
| 13. | Purified water | Remainder |

(note 1)
ES-5300, manufactured by Dow Corning Toray Co., Ltd. was used.
(note 2)
Dispersion TP3 described in the Practical Examples was used.

(Production Method)
Step 1: Components 1 to 9 were mixed.
Step 2: Components 10 to 13 were mixed.
Step 3: Add the aqueous phase obtained in Step 2 to the mixture obtained in Step 1 while agitating. After emulsifying, fill a container with the emulsion to obtain the product.

Formulation Example 4 is a sunscreen cream comprising a dispersion of an inorganic ultraviolet light blocking component treated using the co-modified polyorganosiloxane P3 according to the present invention. Even though this sunscreen cream has a high aqueous phase component content and contains an inorganic ultraviolet light blocking component, there is no separation of the oil components or the powder. Thus, this sunscreen cream can be kept in stock over an extended period of time at a temperature of around 40° C. (ambient temperature during summer) and stability over time is superior. Furthermore, when used, spreadability was excellent, stickiness was reduced and sensation during use was superior. The sunscreen cream was non-irritating, and long-lasting ultraviolet light protection effects were provided. There was no change in this excellent sensation during use from before storing at around 40° C. to after storing.

| Formulation Example 5: Sunscreen (shaking type) (Components) | |
|---|---|
| 1. Octyl methoxycinnamate | 8 parts |
| 2. Octyl palmitate | 7 parts |
| 3. Diethylamino hydroxybenzoyl hexyl benzoate | 2 parts |
| 4. Titanium oxide slurry (note 1) | 25 parts |
| 5. Cyclopentasiloxane | 18.2 parts |
| 6. Dimethicone crosspolymer | 3 parts |
| 7. Trimethylsiloxysilicate | 3.3 part |
| 8. Polyether-modified silicone (note 2) | 1.5 parts |
| 9. Preservative | 0.1 parts |
| 10. Ethanol | 5 parts |
| 11. 1,3-Butylene glycol | 3 parts |
| 12. Purified water | Remainder |

(note 1)
Dispersion TP3 described in the Practical Examples was used.
(note 2)
ES-5300, manufactured by Dow Corning Toray Co., Ltd. was used.

(Production Method)
Step 1: Components 1 to 9 were mixed.
Step 2: Add the mixture of components 10 to 12 to the mixture of step 1 and emulsify.

The obtained sunscreen had reduced stickiness and superior sensation during use when applied on skin, and provided lasting ultraviolet light protection effects.

| Formulation Example 6: Base cream (Components) | |
|---|---|
| 1. Dimethylpolysiloxane (2 mm$^2$/s) | 2 parts |
| 2. Decamethyl cyclopentasiloxane | 10 parts |
| 3. Polyether-modified silicone (note 1) | 2 parts |
| 4. Cetyl isooctanoate | 5 parts |
| 5. Co-modified organopolysiloxane P2 | 0.5 parts |
| 6. 2-Ethylhexyl para-methoxycinnamate | 2 parts |
| 7. Silicone elastomer (note 2) | 4 parts |
| 8. Silicone-treated titanium oxide | 6 parts |
| 9. Silicone-treated red iron oxide | 0.3 parts |
| 10. Silicone-treated yellow iron oxide | 0.7 parts |
| 11. Silicone-treated black iron oxide | 0.07 parts |
| 12. Organomodified bentonite | 0.5 parts |
| 13. Barium sulfate | 2 parts |
| 14. Talc | 1 part |
| 15. Nylon powder | 3 parts |
| 16. Preservative | q.s. |
| 17. Xanthan gum | 0.1 parts |
| 18. L-Ascorbic acid magnesium phosphate ester | 0.3 parts |
| 19. Purified water | Remainder |

(note 1)
ES-5612, manufactured by Dow Corning Toray Co., Ltd., was used.
(note 2)
9045 Silicone Elastomer Blend, manufactured by Dow Corning Corporation, was used.

(Production Method)
Step 1: Mix and disperse components 1 to 15.
Step 2: Components 16 to 19 were mixed.
Step 3: Add the mixture obtained in Step 2 to the mixture obtained in Step 1 and emulsify at room temperature. Fill a container with the emulsion to obtain the product.

This foundation cream demonstrated good spread, and excellent cosmetic film uniformity and adhesion to the skin. Additionally, skin imperfections, wrinkles, and pores were hardly noticeable. Moreover, the emulsion state of the base cream was stable.

| Formulation Example 7: Rouge (Components) | |
|---|---|
| 1. Triethylhexanoin | 10.0 parts |
| 2. Cetyl ethylhexanoate | 17.0 parts |
| 3. Sorbitan sesquiisostearate | 4.0 parts |
| 4. Microcrystalline wax | 10.0 parts |
| 5. Paraffin wax | 15.0 parts |
| 6. Diisostearyl malate | 7.0 parts |
| 7. Glyceryl triisostearate | 9.0 parts |
| 8. Propylene glycol dicapyrlate | 7.0 parts |
| 9. Inulin stearate (product name: Rheopearl ISL2 manufactured by Chiba Flour Milling Co., Ltd.) | 2.0 parts |
| 10. Co-modified organopolysiloxane P3 | 1.0 parts |
| 11. Polyether-modified silicone (note 1) | 2.0 parts |
| 12. Isododecane/(acrylate/polytrimethylsiloxy methacrylate) copolymer (note 2) | 3.0 parts |
| 13. Dimethylpolysiloxane (100 cst) solution of trimethylsiloxysilicic acid (active ingredient: 33%) | 2.0 parts |
| 14. Yellow No. 4 | q.s. |
| 15. Titanium oxide | 1.0 parts |
| 16. Black iron oxide | 1.0 parts |
| 17. Mica | 1.0 parts |
| 18. Red 104 | q.s. |
| 19. Purified water | 7.0 parts |
| 20. 1,3-Butylene glycol | 1.0 parts |
| 21. Preservative | q.s. |
| 22. Perfume | q.s. |

(note 1)
ES-5300, manufactured by Dow Corning Toray Co., Ltd. was used.
(note 2)
FA-4002ID, manufactured by Dow Corning Toray Co., Ltd. was used.

(Production Method)
Step 1: Heat and dissolve components 1 to 18.
Step 2: Components 19 to 21 were mixed.
Step 3: Add the mixture of Step 2 to the mixture of Step 1 and further agitate and mix.
Step 4: Add component 22 to the mixture of Step 3. Fill a closed vessel with the obtained mixture to obtain the product.

The rouge had a luxurious feel and excellent spreadability, could be applied uniformly to the lips, and could deliver a finish having superior luster and feeling of sheerness. Furthermore, there was no stickiness on the lips after application, and storage stability in cases where the product was stocked was excellent.

Formulation Example 8: Liquid rouge
(Components)

| | |
|---|---|
| 1. Phenylmethyl silicone | 10 parts |
| 2. Isopropyl myristate | 10 parts |
| 3. Cyclopentacyloxane/(acrylate/polytrimethylsiloxy methacrylate) copolymer (note 1) | 5 parts |
| 4. Aerosol silicic anhydride | 0.1 parts |
| 5. Spherical urethane powder | 5 parts |
| 6. Cyclopentasiloxane/trimethylsiloxy cinnamic acid (note 2) | 5 parts |
| 7. Co-modified organopolysiloxane P2 | 1 part |
| 8. Polyether-modified silicone (note 3) | 1.5 parts |
| 9. Octyl methoxycinnamate | 1 part |
| 10. Red No. 202 | 0.5 parts |
| 11. Titanium oxide | 0.5 parts |
| 12. Titanated mica | 3 parts |
| 13. Perfume | 0.1 parts |
| 14. Ethanol | 10 parts |
| 15. Preservative | 0.2 parts |
| 16. Sodium chloride | 0.1 parts |
| 17. Purified water | Remainder |

(note 1)
FA-4001CM, manufactured by Dow Corning Toray Co., Ltd. was used.
(note 2)
BY11-018, manufactured by Dow Corning Toray Co., Ltd. was used.
(note 3)
ES-5300, manufactured by Dow Corning Toray Co., Ltd. was used.

(Production Method)
A: Disperse and mix components 1 to 12.
B: Separately, components 13 to 17 were dissolved uniformly.
C: B was added to A and emulsified. After the mixture was defoamed, a water-in-oil emulsion lipstick was obtained by filling a container with the mixture.

Formulation 9: Lipstick
(Components)

| | |
|---|---|
| 1. Polyethylene-polypropylene copolymer | 5 parts |
| 2. Candelilla wax | 5 parts |
| 3. Carnauba wax | 5 parts |
| 4. Vaseline | 10 parts |
| 5. 2-Cetyl ethylhexanoate | 10 parts |
| 6. Diglycerin diisostearate | 14.5 parts |
| 7. Macadamia nut oil | 7 parts |
| 8. Inulin stearate (Rheopearl ISK2 manufactured by Chiba Flour Milling Co., Ltd.) | 23 parts |
| 9. Co-modified organopolysiloxane P3 | 2 parts |
| 10. Red No. 201 | 1 part |
| 11. Red No. 202 | 3 parts |
| 12. Yellow No. 4 aluminum lake | 3 parts |
| 13. Titanium oxide | 1 part |
| 14. Black iron oxide | 0.5 parts |
| 15. Iron oxide titanated mica | 10 parts |
| 16. Preservative | q.s. |
| 17. Perfume | q.s. |

Formulation Example 10: Eye shadow
(Components)

| | |
|---|---|
| 1. Dimethylpolysiloxane (2 cs) | 13 parts |
| 2. Dimethylpolysiloxane (6 cs) | 12 parts |
| 3. Co-modified organopolysiloxane P2 | 1 part |
| 4. PEG10-dimethicone | 1 part |
| 5. Silicone-treated titanium oxide | 6.2 parts |
| 6. Silicone-treated sericite | 4 parts |
| 7. Silicone-treated mica | 6 parts |
| 8. Microcrystalline wax | 2 parts |
| 9. Candelilla wax | 1 part |
| 10. Dimethylsilylated silica | 2 parts |
| 11. Sodium chloride | 2 parts |
| 12. Propylene glycol | 8 parts |
| 13. Preservative | q.s. |
| 14. Perfume | q.s. |
| 15. Purified water | remainder |

(Production Method)
A: Components 1 to 10 are added and dispersed uniformly.
B: Components 11 to 15 were dissolved uniformly.
C: B was gradually added to A and emulsified while stirring to obtain an eye shadow.

The obtained eye shadow spread smoothly when applying and had superior color development.

Formulation Example 11: Mascara
(Components)

| | |
|---|---|
| 1. Paraffin wax | 5 parts |
| 2. Light liquid isoparaffin | Remainder |
| 3. Caprylyl methicone | 3 parts |
| 4. Trimethylsiloxysilicic acid | 0.5 parts |
| 5. Co-modified organopolysiloxane P3 | 0.5 parts |
| 6. Polyglyceryl diisostearate | 3 parts |
| 7. Trioctanoin | 6 parts |
| 8. Dimethicone | 5 parts |
| 9. Organomodified bentonite | 2 parts |
| 10. Cyclopentasiloxane, dimethicone crosspolymer (note 1) | 5 parts |
| 11. Fluorine compound surface-treated black iron oxide | 6 parts |
| 12. Sucrose fatty acid ester | 4 parts |
| 13. Beeswax | 5 parts |
| 14. Pentaerythrityl rosinate | 5 parts |
| 15. Preservative | q.s. |
| 16. Polyvinylalcohol | 1 part |
| 17. Purified water | 30 parts |

(note 1)
DC-9040, manufactured by Dow Corning Corporation, was used.

(Production Method)
After components 1 to 14 were dissolved while heating, the components were sufficiently mixed and dispersed. A mixture of components 15 to 17 was added to this mixture and emulsified, and a product was obtained by filling a container with the mixture.

The resulting mascara had a deep dark appearance and excellent sheen when used. In addition, the mascara demonstrated good adhesion to the eyelashes and an excellent eyelash curl volume effect which lasted a long time.

Products produced by replacing the components corresponding with silicone compounds Nos. 1 to 14 in the Formulation Examples of the cosmetic compositions recited in Patent Document 5 (WO/2011/049248, filed by the present applicant) with the co-modified organopolysiloxanes (co-modified organopolysiloxanes P1 to P3) according to the present invention are included in the scope of the present invention as Formulation Examples of cosmetic compositions according to the present invention.

Specifically, the aforementioned Patent Document 5 discloses emulsions, lip glosses, oil-based foundations, water-in-oil emulsion transparent anti-perspirant compositions, and non-aqueous stick-form anti-perspirant compositions as compositions that can be replaced by the co-modified organopolysiloxane according to the present invention, and paragraphs [0459] to in the above-mentioned Patent Document 5 also disclose the following formulation examples.

[Example 1: Emulsion foundation]
[Example 2: Liquid foundation]
[Example 3: Foundation]
[Example 4: Water-in-oil cream]
[Example 5: Water-in-oil emulsion composition]
[Example 6: Water-in-oil emulsion rouge (liquid)]
[Example 7: Liquid rouge]
[Example 8: Rouge]
[Example 9: Sunscreen emulsion]
[Example 10: Emulsion]
[Example 11: UV blocking cream]
[Example 12: UV blocking water-in-oil emulsion]
[Example 13: Sunscreen agent]
[Example 14: Water-in-oil emulsion sunscreen]
[Example 15: O/W cream]
[Example 16: Eye shadow]
[Example 17: Mascara]
[Example 18: Mascara]
[Example 19: Solid powder eye shadow]
[Example 20: Pressed powder cosmetic]
[Example 21: Powder foundation]
[Example 22: Pressed foundation]
[Example 23: Cream]
[Example 24: Foundation]
[Example 25: Water-in-oil emulsion-type sunscreen]
[Example 26: Lipstick]
[Example 27: Rouge]
[Example 28: Foundation]
[Example 29: Anti-perspirant aerosolized cosmetic composition]
[Example 30: Nonaqueous pressurized anti-perspirant product]
[Example 31: Aerosol type anti-perspirant composition]
[Example 32: Anti-perspirant lotion composition]
[Example 33: W/O emulsion-type skin external use preparation]
[Example 34: Nonaqueous anti-perspirant deodorant stick composition]
[Example 35: W/O solid anti-perspirant stick composition]
[Example 36: W/O emulsion type anti-perspirant cream composition]
[Example 37: Mascara]
[Example 38: Aftershave cream]
[Example 39: Solid foundation]
[Example 40: Daytime use skin-lightening cream]
[Example 41: Sun tanning cream]
[Example 42: Polyol/O-type nonaqueous emulsion skin external use preparation]
[Example 43: Polyol/O-type nonaqueous emulsion skin external use preparation]

INDUSTRIAL APPLICABILITY

The co-modified organopolysiloxane according to the present invention can be supplied at a relatively low cost even on an industrial scale, in particular, and has excellent surface treating performance and surface activity, so the co-modified organopolysiloxane can be used in external use preparations and, in particular, for industrial applications other than cosmetics. Examples thereof include varnishes or coating additives having superior heat resistance, weather resistance, or electrical properties; foam stabilizers or modifying agents for polyol base compounds used in various urethane and foam materials; debonding agents or release agents; antifoaming agents; grease or oil compounds; modifying agents, additives, or surface treatment agents use for oil, rubber, or resin of insulating, glazing, water repelling, heating mediums, cooling mediums, and lubricants; compounds, modifying agents, and precursors for silane coupling agents; coating materials or sealing materials for buildings or linings; protective agents, lubricants, or buffer agents for fiber optics and electrical wiring; and the like. However, the novel organopolysiloxane copolymer according to the present invention is not limited to such applications.

The invention claimed is:

1. A co-modified organopolysiloxane having a group ($L^1$) having a siloxane dendron structure and a group (Q) containing a saccharide component of formula (1)

$$R^1_a R^2_b L^1_c Q_d SiO_{(4-a-b-c-d)/2} \quad (1)$$

wherein
  each $R^1$ is independently a substituted or unsubstituted monovalent hydrocarbon group having from 1 to 30 carbon atoms, or a hydrogen atom;
  each $R^2$ is independently a substituted or unsubstituted straight-chain or branched monovalent hydrocarbon group having from 6 to 30 carbon atoms, or a chainlike organosiloxane group of formula (2-1);

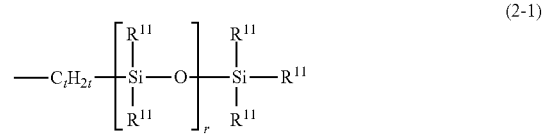

(2-1)

wherein each $R^{11}$ is independently a substituted or unsubstituted monovalent hydrocarbon group having from 1 to 30 carbon atoms, a hydroxyl group, or a hydrogen atom, with at least one of the $R^{11}$ moieties being the monovalent hydrocarbon group; t is a number in a range of 2 to 10; and r is a number in a range of 1 to 500; or of formula (2-2) below:

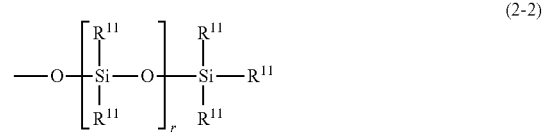

(2-2)

wherein $R^{11}$ and r are defined above; and
  $L^1$ represents a silylalkyl group having a siloxane dendron structure of formula (3) when i=1;

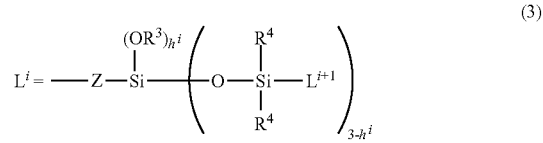

(3)

wherein each $R^3$ independently represents a substituted or unsubstituted, straight or branched monovalent hydrocarbon group having from 1 to 30 carbon atoms; $R^4$ each independently represents an alkyl group having from 1 to 6 carbon atoms or phenyl group; Z represents a divalent organic group; i represents a generation of the aforementioned silylalkyl group represented by $L^i$ and is an integer of 1 to k when k is a number of generations that is a number of repetitions of the silylalkyl group; the number of generations k is an integer from 1 to 10; $L^{i+1}$ is the silylalkyl group when i is less than k, and $R^4$ when i=k, and $h^i$ is a number in a range from 0 to 3;

Q is a group containing a saccharide component of formula $X\text{-}(G^1)_n\text{-}(G^2)_m$, wherein $G^1$ is a saccharide component having from 5 to 12 carbon atoms; n+m is from 1 to 10; and n or m may be 0, $G^2$ is a saccharide component having from 5 to 12 carbon atoms which may be additionally substituted with an organic or organic silicon group;

X is a linking group independently selected from the following linking groups:

—$R^5$—NHC(O)—$R^6$—;
—$R^5$—NHC(O)O—$R^6$—;
—$R^5$—NH—C(O)—NH—$R^6$—;
—$R^5$—O—$R^6$—;
—$R^5$—CH(OH)—CH$_2$—O—$R^6$—;
—$R^5$—S—$R^6$—;
—$R^5$—CH(OH)—CH$_2$—NH—$R^6$—; and
—$R^5$—N($R^1$)—$R^6$—;

wherein $R^5$ and $R^6$ are divalent spacer groups containing $(R^a)_u$, $(R^b)_v$, and $(R^c)_x$, where at least one of u, v, and x must be 1; $R^a$ and $R^c$ are alkylene groups having from 1 to 12 carbon atoms or polyoxyalkylene groups of formula $(R^dO)_p$, where $R^d$ is H or has from 1 to 12 carbon atoms; p is any integer from 1 to 50; each $(R^dO)$ moiety may be the same or different; $R^b$ is —N($R^e$)—, where $R^e$ is H, an alkyl group having from 1 to 12 carbon atoms, or X—Y, where X is as defined above or $R^5$, and Y is a carboxylic acid, phosphate, sulfate, sulfonate, or tertiary ammonium group; and a, b, c, and d are numbers in ranges so that $1.0 \le a+b \le 2.5$, $0.001 \le c \le 1.5$, and $0.001 \le d \le 1.5$.

2. The co-modified organopolysiloxane of claim 1, wherein Q is a group containing a saccharide component obtained by a reaction between an amino group and a hydroxy functional saccharide.

3. The co-modified organopolysiloxane of claim 1, wherein Q is a sugar lactone amide alkyl group obtained by a reaction between a silicon-bonded amino group of formula:

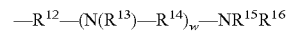
—$R^{12}$—(N($R^{13}$)—$R^{14}$)$_w$—N$R^{15}R^{16}$ wherein
$R^{12}$ is an alkylene group having from 2 to 8 carbon atoms;
$R^{13}$, $R^{15}$, and $R^{16}$ are independently hydrogen atoms or monovalent organic groups having from 1 to 10 carbon atoms, but at least one of all of $R^{13}$, $R^{15}$, and $R^{16}$ is a hydrogen atom;
$R^{14}$ is an alkylene group having from 1 to 4 carbon atoms; and w is a number in a range of $0 \le w \le 6$ and
a sugar lactone compound.

4. The co-modified organopolysiloxane of claim 1, being of formula (1-1)

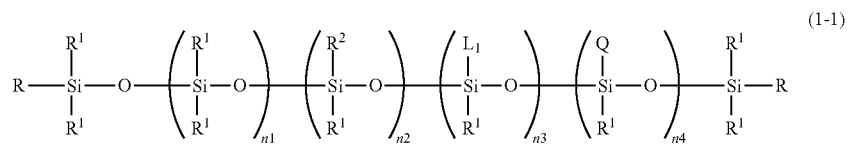

where $R^1$, $R^2$, $L^1$ and Q are defined above, and R is a group selected from $R^1$, $R^2$, $L^1$, and Q; however, when n3=0, at least one R is $L^1$; and when n4=0, at least one R is Q; and (n1+n2+n3+n4) is a number in a range from 0 to 50; n1 is a number in a range from 0 to 45, n2 is a number in a range from 0 to 30, n3 is a number in a range from 0 to 20, and n4 is a number in a range from 0 to 2.

5. The co-modified organopolysiloxane of claim 1, being of formula (1-1-1)

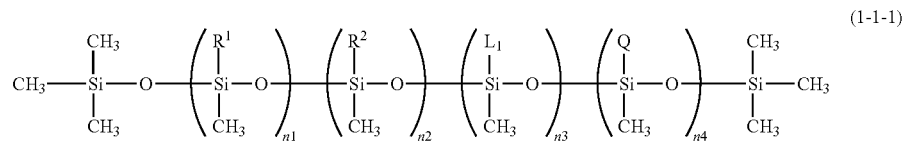

where $R^1$, $R^2$, $L^1$, and Q defined above, (n1+n2+n3+n4) is a number in a range from 2 to 50, n1 is a number in a range from 0 to 45, n2 is a number in a range from 0 to 30, n3 is a number in a range from 1 to 20, and n4 is a number in a range from 0.1 to 2.

6. The co-modified organopolysiloxane of claim 4, wherein
in formula (1-1), $L^1$ is a functional group of formula (2-1) or formula (2-2):

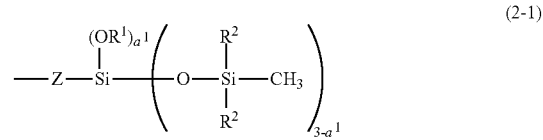

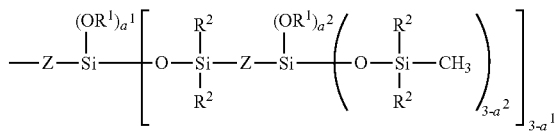
(2-2)

wherein $R^1$, $R^2$, and Z defined above, and $a^1$ and $a^2$ are each independently numbers in a range of 0 to 3;

Q is a sugar lactone amide alkyl group ($Q^1$) obtained by a reaction between a silicon-bonded amino group of formula:

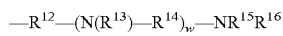

wherein $R^{12}$ is an alkylene group having from 2 to 8 carbon atoms;

$R^{13}$, $R^{15}$, and $R^{16}$ are independently hydrogen atoms or monovalent organic groups having from 1 to 10 carbon atoms, but at least one of $R^{13}$, $R^{15}$, and $R^{16}$ is a hydrogen atom;

$R^{14}$ is an alkylene group having from 1 to 4 carbon atoms; and w is a number in a range of $0 \leq w \leq 6$ and a sugar lactone compound.

7. The co-modified organopolysiloxane of claim 6, being of formula (1-1-A) or formula (1-1-B)

8. A method for producing the co-modified organopolysiloxane of claim 1, the method comprising the following steps (I) to (III):

step (I): producing a co-modified organopolysiloxane intermediate having a functional group that can react with a compound having a saccharide component directly or after a deprotection reaction by co-hydrosilylating: a compound having a siloxane dendron structure;

a compound having a functional group that can react with a compound having a saccharide component directly or after a deprotection reaction; and an organohydrogenpolysiloxane;

step (II): producing a co-modified organopolysiloxane intermediate having a functional group that can react with a compound having a saccharide component by performing a deprotection reaction as necessary on the co-modified organopolysiloxane intermediate obtained in step (I); and step (III): reacting the co-modified organopolysiloxane intermediate obtained in step (I) or step (II) and a compound having a saccharide component to produce the co-modified organopolysiloxane.

9. The method for producing a co-modified organopolysiloxane of claim 8, wherein step (II) is an essential step; and the compound having a functional group that can react with a compound having a saccharide component after a deprotection reaction is an allylamine protected by an organosilyl group.

10. The method for producing a co-modified organopolysiloxane of claim 9, wherein the organosilyl group is a bis-dimethylsilylethylene group.

11. A surface treatment agent comprising the co-modified organopolysiloxane of claim 1.

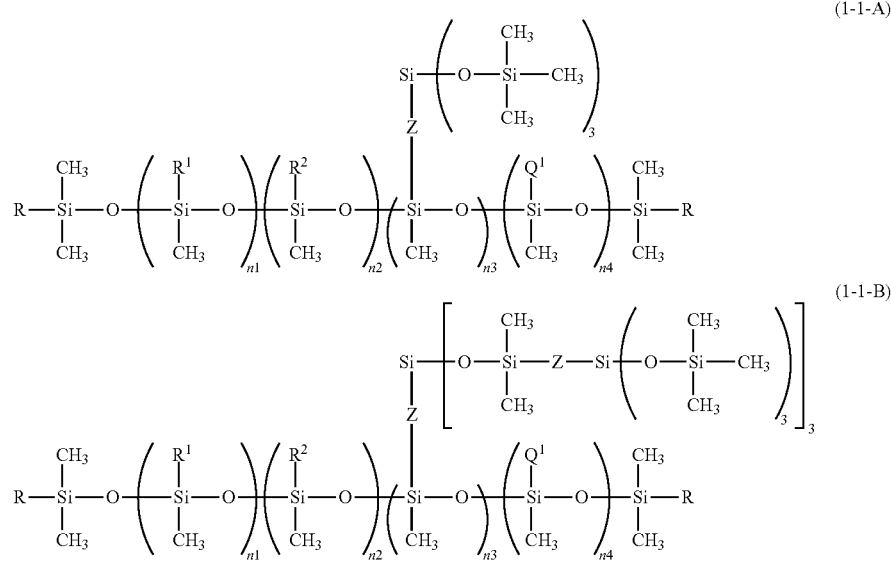

where Z, $R^1$, $R^2$, and $Q^1$ are defined above; R is a group selected from $R^1$, $R^2$, and $L^1$ and $Q^1$; (n1+n2+n3+n4) is a number in a range from 2 to 50; n1 is a number in a range from 0 to 45, n2 is a number in a range from 0 to 30, n3 is a number in a range from 1 to 20, and n4 is a number in a range from 0.1 to 2.

12. A powder treatment agent comprising the co-modified organopolysiloxane of claim 1.

13. A powder composition comprising:
(A) the co-modified organopolysiloxane of claim 1, and
(B) a powder or coloring agent.

14. The powder composition of claim 13, wherein the component (B) is one or more selected from the group consisting of an inorganic pigment powder, an organic pigment powder, and a resin powder, each having an average diameter in a range of 1 nm to 20 μm.

15. A powder-in-oil dispersion comprising:
(A) the co-modified organopolysiloxane of claim 1;
(B) a powder or coloring agent; and (C) one or more oil agents selected from the group consisting of a silicone oil, a nonpolar organic compound, and a low-polarity organic compound that is a liquid at 5 to 100° C.

16. A preparation for external use comprising the co-modified organopolysiloxane of claim 1.

17. The preparation for external use of claim 16, further defined as a cosmetic composition or a medicament.

18. A cosmetic composition comprising the powder composition of claim 13.

19. A cosmetic composition comprising the powder-in-oil dispersion of claim 15.

20. A makeup cosmetic comprising:
 (A) the co-modified organopolysiloxane of claim 1;
 (B) a powder or coloring agent; and
 (C) one or more oil agent selected from the group consisting of a silicone oil, a nonpolar organic compound, and a low polarity organic compound that is liquid from 5° C. to 100° C.

\* \* \* \* \*